United States Patent
Coghill et al.

(10) Patent No.: US 12,208,105 B2
(45) Date of Patent: Jan. 28, 2025

(54) METHODS FOR ATTENUATING GRAFT-VERSUS-HOST DISEASE AND OPPORTUNISTIC INFECTIONS

(71) Applicant: The University of North Carolina at Chapel Hill, Chapel Hill, NC (US)

(72) Inventors: James M. Coghill, Wake Forest, NC (US); Kenneth A. Fowler, Durham, NC (US)

(73) Assignee: The University of North Carolina at Chapel Hill, Chapel Hill, NC (US)

( * ) Notice: Subject to any disclaimer, the term of this patent is extended or adjusted under 35 U.S.C. 154(b) by 867 days.

(21) Appl. No.: 17/298,776

(22) PCT Filed: Dec. 3, 2019

(86) PCT No.: PCT/US2019/064207
§ 371 (c)(1),
(2) Date: Jun. 1, 2021

(87) PCT Pub. No.: WO2020/117782
PCT Pub. Date: Jun. 11, 2020

(65) Prior Publication Data
US 2022/0031711 A1    Feb. 3, 2022

Related U.S. Application Data

(60) Provisional application No. 62/774,646, filed on Dec. 3, 2018.

(51) Int. Cl.
*A61K 31/575* (2006.01)
*A61P 31/22* (2006.01)
*A61P 37/06* (2006.01)

(52) U.S. Cl.
CPC ............ *A61K 31/575* (2013.01); *A61P 31/22* (2018.01); *A61P 37/06* (2018.01)

(58) Field of Classification Search
CPC ......... A61K 31/575; A61P 31/22; A61P 37/06

USPC ........................................................ 514/169
See application file for complete search history.

(56) References Cited

U.S. PATENT DOCUMENTS

2003/0212045 A1    11/2003    Cushman et al.
2016/0228413 A1    8/2016    Bridger et al.

FOREIGN PATENT DOCUMENTS

WO    2011097607 A1    8/2011

OTHER PUBLICATIONS

"International Search Report and Written Opinion corresponding to International Application No. PCT/US2019/064207 mailed Mar. 20, 2020".
Fowler, K. A. et al., "The Anti-Viral Compound Cosalane Attenuates Acute Graft-Versus-Host Disease in Murine Hematopoietic Stem Cell Transplant Models", Blood (Experimental Transplantation: Basic Biology, Pre-Clinical Models: Poster II). 130:Supp 1 (Dec. 2017).
Hull-Ryde, E. A. et al., "Identification of Cosalane as an Inhibitor of Human and Murine CC?Chemokine Receptor 7 Signaling via a High-Throughput Screen". SLAS Discovery, 23: 1083-1091 (Jun. 2018).
Fowler, K. et al., "The Ex Vivo Treatment of Donor T Cells with Cosalane, an HIV Therapeutic and Small-Molecule Antagonist of CC-Chemokine Receptor 7, Separates Acute Graft-versus-Host Disease from Graft-versus-Leukemia Responses in Murine Hematopoietic Stem Cell Transplantation Models", Biol Blood Marrow Transplant, 25:1062-1074 (Jan. 2019).
"International Preliminary Report on Patentability corresponding to International Application No. PCT/US2019/064207 mailed Jun. 17, 2021".

*Primary Examiner* — Kristin A Vajda
(74) *Attorney, Agent, or Firm* — Myers Bigel, P.A.

(57) ABSTRACT

The present invention relates to methods for attenuating graft-versus-host disease after transplantation of a graft comprising hematopoietic stem cells in a subject. The invention further relates to methods of limiting opportunistic microbial infections in a subject after transplantation of a graft comprising hematopoietic stem cells.

10 Claims, 11 Drawing Sheets

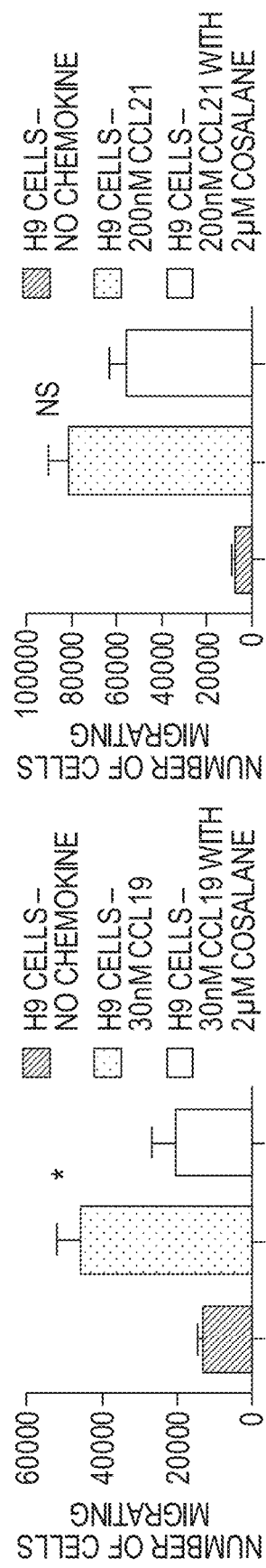
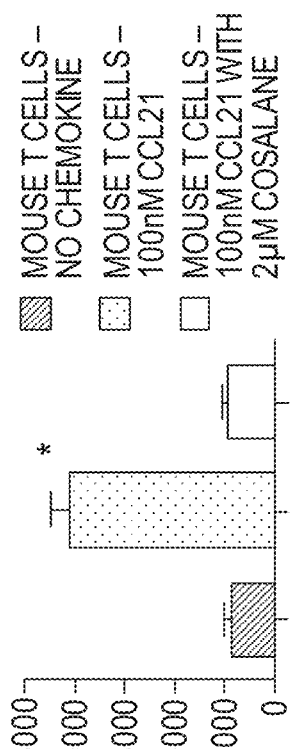
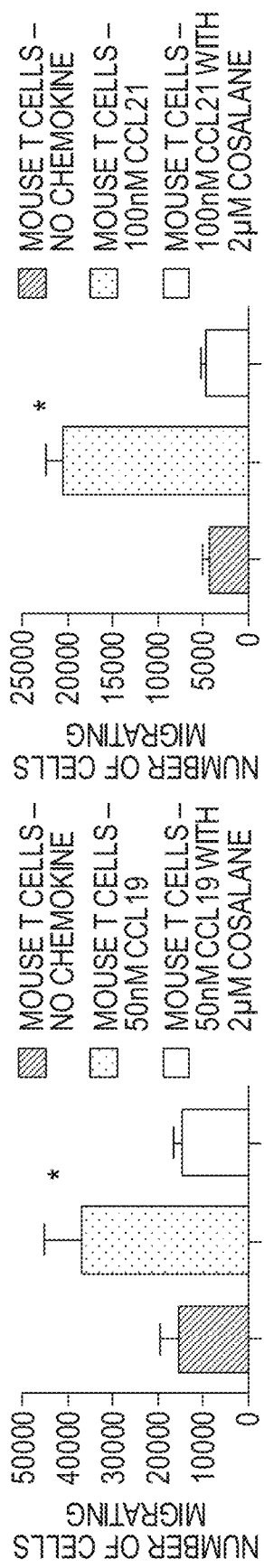

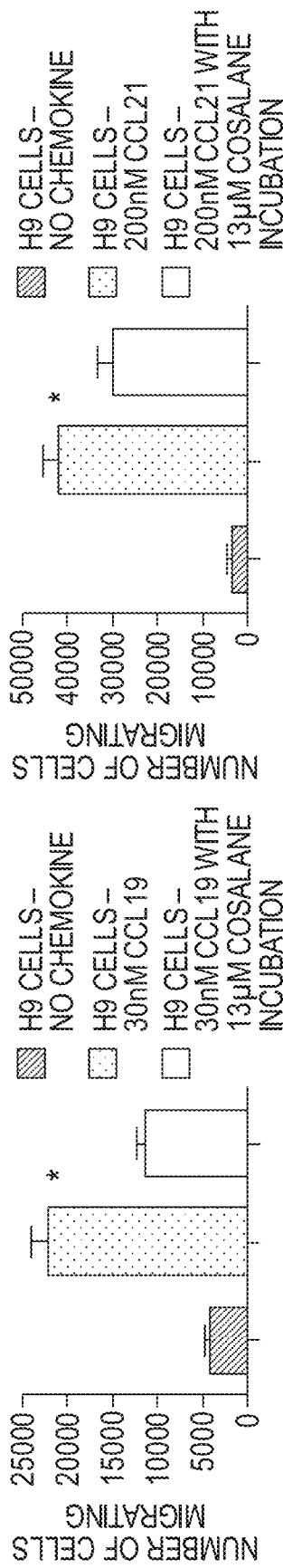
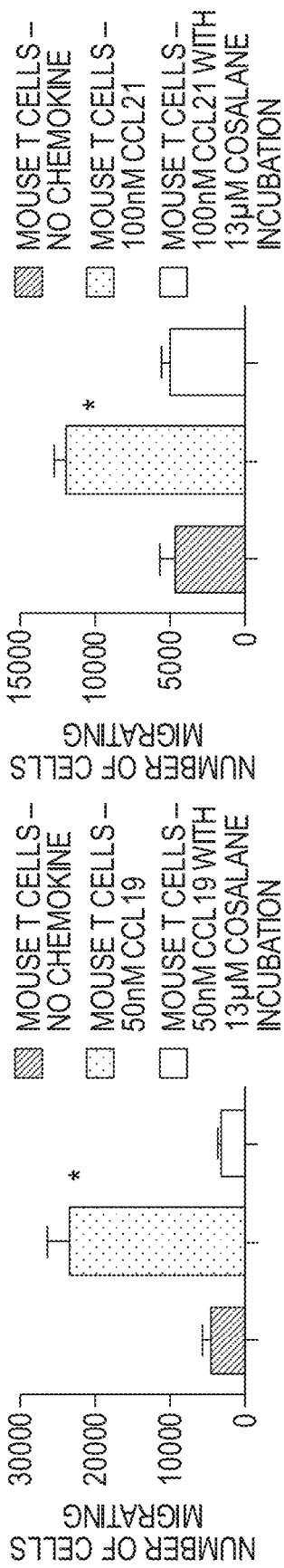

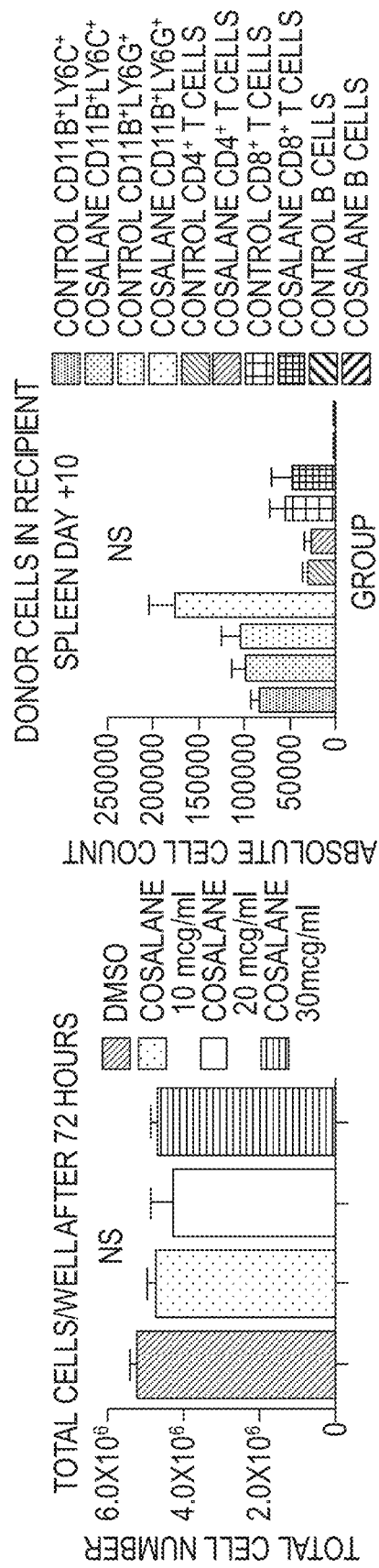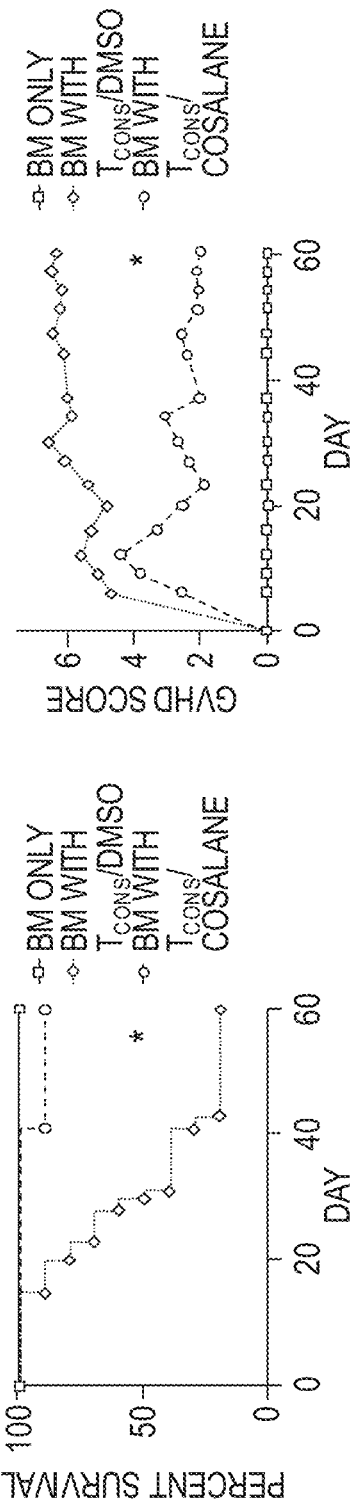
FIG. 4A
FIG. 4B
FIG. 4C
FIG. 4D

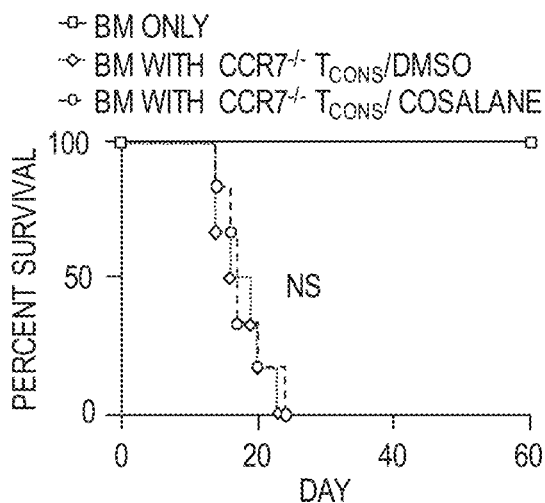 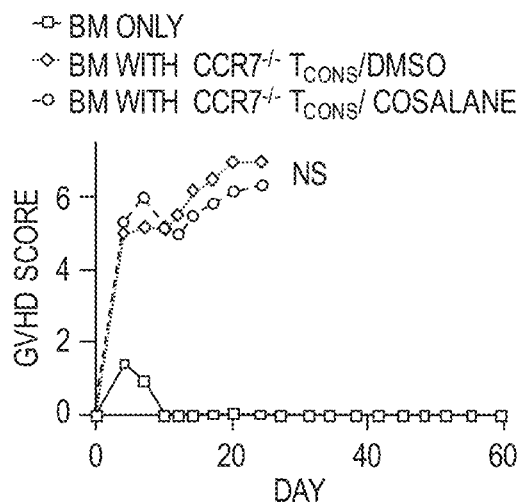
FIG. 7A   FIG. 7B
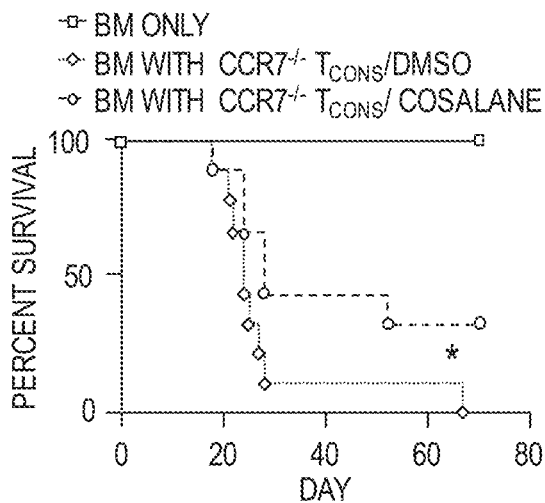 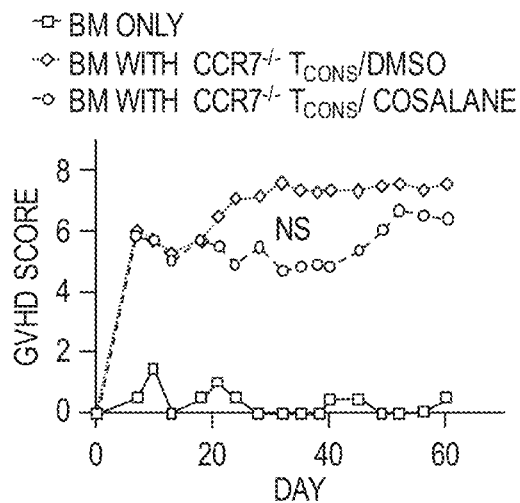
FIG. 7C   FIG. 7D
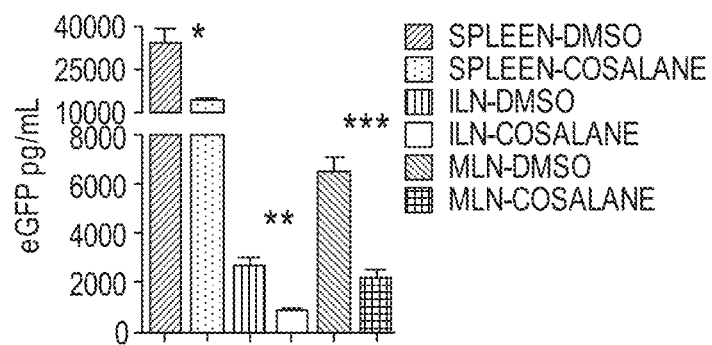
FIG. 7E

METHODS FOR ATTENUATING GRAFT-VERSUS-HOST DISEASE AND OPPORTUNISTIC INFECTIONS

STATEMENT OF PRIORITY

This application claims the benefit of U.S. Provisional Application Ser. No. 62/774,646, filed Dec. 3, 2018, the entire contents of which are incorporated by reference herein.

STATEMENT OF GOVERNMENT SUPPORT

This application is a 35 U.S.C. § 371 national phase application of PCT Application PCT/US2019/064207 filed Dec. 3, 2019, which claims the benefit, under 35 U.S.C. § 119 (e), of U.S. Provisional Application Ser. No. 62/774,646, filed on Dec. 3, 2018, the entire contents of each of which are incorporated by reference herein.

FIELD OF THE INVENTION

The present invention relates to methods for attenuating graft-versus-host disease after transplantation of a graft comprising hematopoietic stem cells in a subject. The invention further relates to methods of limiting opportunistic microbial infections in a subject after transplantation of a graft comprising hematopoietic stem cells.

BACKGROUND OF THE INVENTION

Allogeneic hematopoietic stem cell transplantation (HSCT) is a powerful therapeutic modality that has generated sustained complete remissions in patients with hematologic malignancies rarely curable with conventional chemotherapy alone. HSCT offers several advantages over traditional cytotoxic regimens. First, higher doses of chemotherapy can be administered in an attempt to overcome any drug resistance displayed by the cancer cells, since the resulting myelosuppression is avoided by the subsequent administration of stem cells from a healthy donor. Second and perhaps more importantly, mature T cells contained in the graft are able to mount potent immune responses against residual cancer cells due to major and/or minor major histocompatibility complex (MHC) disparities between the donor and recipient.

Unfortunately, the allo-immune responses driving this graft-versus-leukemia (GVL) effect are not specific for malignant cells. As a consequence, donor T cells attack normal host tissues, resulting in a process known as graft-versus-host disease (GVHD). GVHD is classified into two forms, acute and chronic, based on the nature of the tissue injury that is observed. Acute GVHD (aGVHD) is primarily a T cell driven process, usually occurring within the first few months after transplant, and is characterized by an intense inflammatory reaction. Common manifestations include a severe, sometimes blistering skin rash, profound diarrhea, cholestatic liver damage, and on occasion acute lung injury. With time, aGVHD can develop into a more chronic, B cell associated process that is usually more fibrotic and widespread.

Currently, transplant physicians rely on calcineurin inhibitors, anti-metabolites, and T cell depleting antibodies to prevent aGVHD. These agents are not always effective, however, with about 50% of patients developing aGVHD despite prophylactic immunosuppression. Further, they are not specific for aGVHD, and can compromise beneficial anti-tumor immunity or predispose a patient to infection. For patients who do develop aGVHD, therapy usually consists of high doses of corticosteroids, a treatment associated with numerous complications. For those patients not responding to steroids, outcomes are dismal, with mortality rates approaching 70% in some series.

There remains a need for more effective and specific therapies for GVHD.

SUMMARY OF THE INVENTION

The present invention is based, in part, on the finding that the compound cosalane acts as an antagonist of the lymphoid trafficking receptor CCR7 and attenuates aGVHD. This activity, along with the antiviral activity for which cosalane was originally developed, may be used advantageously to control the occurrence of GVHD (e.g., aGVHD) and/or opportunistic microbial infections after transplantation of grafts comprising hematopoietic stem cells (HSC) into a subject. An additional advantage of the present invention is the ability to inhibit GVHD while maintaining the ability of the graft to exert an anti-cancer response, e.g., a graft-versus-leukemia response.

Accordingly, one aspect of the invention relates to a method for modifying HSC to decrease the risk of developing graft versus host disease following transplantation of the cells into a subject, comprising contacting the HSC with an effective amount of a compound of Formula I or Formula II or a pharmaceutically acceptable salt thereof:

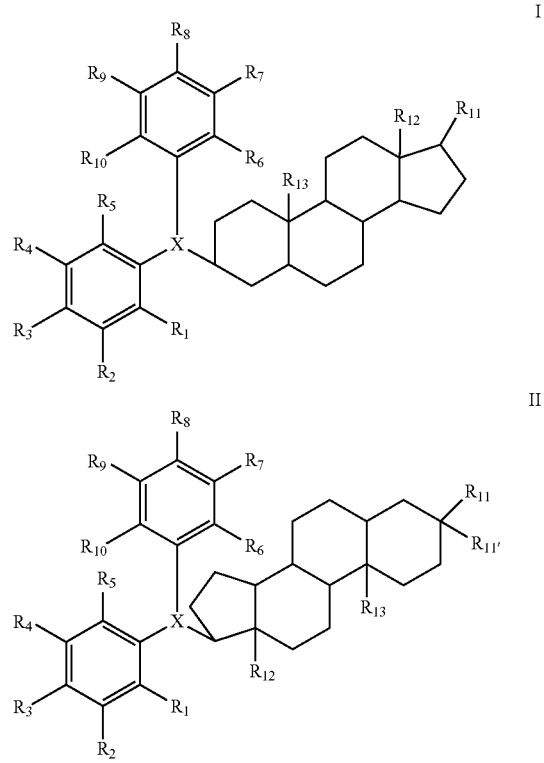

wherein
$R_1$ to $R_{11}$ and $R_{11'}$ are independently H, halogen, hydroxy, amino, $C_1$-$C_5$ alkoxy, benzoyloxy, $R_{14}C(O)O$, COOH or a salt thereof, $SO_3H$ or a salt thereof, $PO_3H_2$ or a salt thereof, $C_1$-$C_{24}$ alkyl, $COOR_{15}$, $SO_3R_{16}$, C(O)

$NR_{17}R_{18}$, $SO_2NR_{19}R_{20}$, $SR_{21}$, $SCH_2R_{25}$, $SC(O)R_{21}$, $NR_{22}R_{23}$, $NHC(O)$—$R_{24}$, $O(CH_2)_n$—$R_{26}$—$R_{27}$, $OC(O)N(H)C(H)(R_{28})COOR_{29}$;

$R_{12}$ and $R_{13}$ are $C_1$-$C_7$ alkyl groups;
$R_{14}$ is H or $C_1$-$C_5$ alkyl;
$R_{15}$ is aryl or $C_1$-$C_5$ alkyl;
$R_{16}$ is aryl or $C_1$-$C_5$ alkyl;
$R_{17}$ and $R_{18}$ are each independently H, $C_1$-$C_5$ alkyl, aryl or hydroxy;
$R_{19}$ and $R_{20}$ are each independently H, $C_1$-$C_5$ alkyl or aryl;
$R_{21}$ is $C_1$-$C_5$ alkyl or aryl;
$R_{22}$ and $R_{23}$ are each independently H, $C_1$-$C_5$ alkyl or aryl;
$R_{24}$ is aryl optionally substituted with COOH or a salt thereof, or $C_1$-$C_7$ alkoxy;
$R_{25}$ is aryl;
$R_{26}$ is aryl;
$R_{27}$ is COOH or a salt thereof, $B(OH)_2$ or a salt thereof, nitro, $C_1$-$C_7$ alkoxy or aryl, wherein the aryl is substituted with COOH or a salt thereof, $B(OH)_2$ or a salt thereof, nitro or $C_1$-$C_7$ alkoxy;
$R_{28}$ is an amino acid side chain;
$R_{29}$ is H or a $C_1$-$C_4$ alkyl;
X is a ($C_1$-$C_7$ alkylene) or ($C_1$-$C_7$ alkylene)C(O)NH; and n is 1 to 7;
thereby decreasing the risk of developing graft versus host disease following transplantation of the cells.

Another aspect of the invention relates to a method for decreasing the risk of developing graft versus host disease following transplantation of a graft comprising HSC in a subject in need thereof, comprising contacting the graft with an effective amount of a compound of Formula I or Formula II or a pharmaceutically acceptable salt thereof:

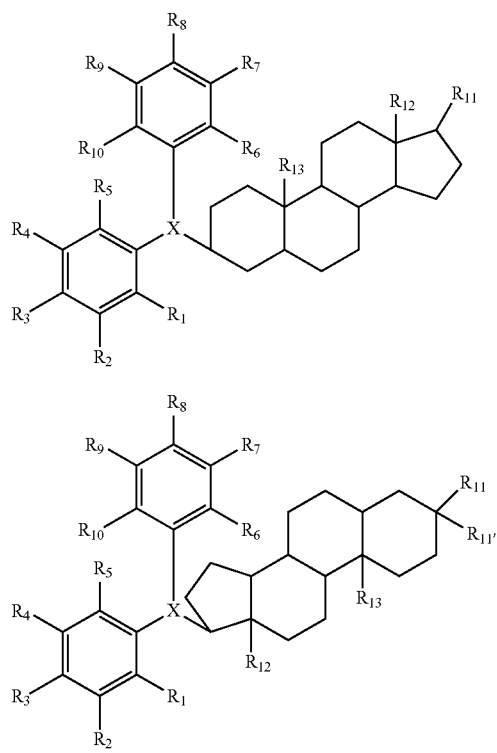

wherein
$R_1$ to $R_{11}$ and $R_{11'}$ are independently H, halogen, hydroxy, amino, $C_1$-$C_5$ alkoxy, benzoyloxy, $R_{14}C(O)O$, COOH or a salt thereof, $SO_3H$ or a salt thereof, $PO_3H_2$ or a salt thereof, $C_1$-$C_{24}$ alkyl, $COOR_{15}$, $SO_3R_{16}$, $C(O)NR_{17}R_{18}$, $SO_2NR_{19}R_{20}$, $SR_{21}$, $SCH_2R_{25}$, $SC(O)R_{21}$, $NR_{22}R_{23}$, $NHC(O)$—$R_{24}$, $O(CH_2)_n$—$R_{26}$—$R_{27}$, $OC(O)N(H)C(H)(R_{28})COOR_{29}$;

$R_{12}$ and $R_{13}$ are $C_1$-$C_7$ alkyl groups;
$R_{14}$ is H or $C_1$-$C_5$ alkyl;
$R_{15}$ is aryl or $C_1$-$C_5$ alkyl;
$R_{16}$ is aryl or $C_1$-$C_5$ alkyl;
$R_{17}$ and $R_{18}$ are each independently H, $C_1$-$C_5$ alkyl, aryl or hydroxy;
$R_{19}$ and $R_{20}$ are each independently H, $C_1$-$C_5$ alkyl or aryl;
$R_{21}$ is $C_1$-$C_5$ alkyl or aryl;
$R_{22}$ and $R_{23}$ are each independently H, $C_1$-$C_5$ alkyl or aryl;
$R_{24}$ is aryl optionally substituted with COOH or a salt thereof, or $C_1$-$C_7$ alkoxy;
$R_{25}$ is aryl;
$R_{26}$ is aryl;
$R_{27}$ is COOH or a salt thereof, $B(OH)_2$ or a salt thereof, nitro, $C_1$-$C_7$ alkoxy or aryl, wherein the aryl is substituted with COOH or a salt thereof, $B(OH)_2$ or a salt thereof, nitro or $C_1$-$C_7$ alkoxy;
$R_{28}$ is an amino acid side chain;
$R_{29}$ is H or a $C_1$-$C_4$ alkyl;
X is a ($C_1$-$C_7$ alkylene) or ($C_1$-$C_7$ alkylene)C(O)NH; and n is 1 to 7; and
transplanting the contacted graft into the subject;
thereby decreasing the developing risk of graft versus host disease.

A further aspect of the invention relates to a method for decreasing the risk of microbial infection after transplantation of a graft comprising HSC in a subject in need thereof, comprising administering to the subject an effective amount of a compound of Formula I or Formula II or a pharmaceutically acceptable salt thereof:

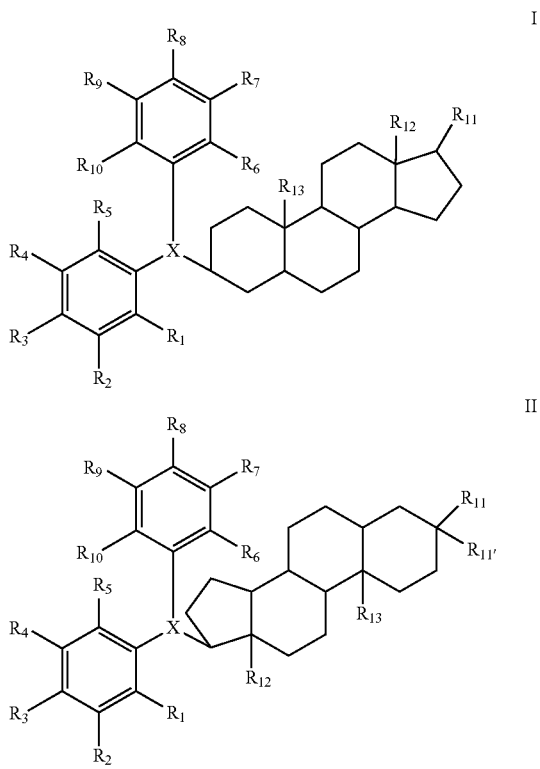

wherein
- $R_1$ to $R_{11}$ and $R_{11'}$ are independently H, halogen, hydroxy, amino, $C_1$-$C_5$ alkoxy, benzoyloxy, $R_{14}C(O)O$, COOH or a salt thereof, $SO_3H$ or a salt thereof, $PO_3H_2$ or a salt thereof, $C_1$-$C_{24}$ alkyl, $COOR_{15}$, $SO_3R_{16}$, $C(O)NR_{17}R_{18}$, $SO_2NR_{19}R_{20}$, $SR_{21}$, $SCH_2R_{25}$, $SC(O)R_{21}$, $NR_{22}R_{23}$, NHC(O)—$R_{24}$, $O(CH_2)_n$—$R_{26}$—$R_{27}$, $OC(O)N(H)C(H)(R_{28})COOR_{29}$;
- $R_{12}$ and $R_{13}$ are $C_1$-$C_7$ alkyl groups;
- $R_{14}$ is H or $C_1$-$C_5$ alkyl;
- $R_{15}$ is aryl or $C_1$-$C_5$ alkyl;
- $R_{16}$ is aryl or $C_1$-$C_5$ alkyl;
- $R_{17}$ and $R_{18}$ are each independently H, $C_1$-$C_5$ alkyl, aryl or hydroxy;
- $R_{19}$ and $R_{20}$ are each independently H, $C_1$-$C_5$ alkyl or aryl;
- $R_{21}$ is $C_1$-$C_5$ alkyl or aryl;
- $R_{22}$ and $R_{23}$ are each independently H, $C_1$-$C_5$ alkyl or aryl;
- $R_{24}$ is aryl optionally substituted with COOH or a salt thereof, or $C_1$-$C_7$ alkoxy;
- $R_{25}$ is aryl;
- $R_{26}$ is aryl;
- $R_{27}$ is COOH or a salt thereof, $B(OH)_2$ or a salt thereof, nitro, $C_1$-$C_7$ alkoxy or aryl, wherein the aryl is substituted with COOH or a salt thereof, $B(OH)_2$ or a salt thereof, nitro or $C_1$-$C_7$ alkoxy;
- $R_{28}$ is an amino acid side chain;
- $R_{29}$ is H or a $C_1$-$C_4$ alkyl;
- X is a ($C_1$-$C_7$ alkylene) or ($C_1$-$C_7$ alkylene)C(O)NH; and
- n is 1 to 7;

thereby decreasing the risk of microbial infection.

In each of the methods of the invention, the compound of Formula I or Formula II may be cosalane or a variant or derivative thereof or a pharmaceutically acceptable salt or prodrug thereof.

Each of the methods of the invention may be carried out ex vivo, in vivo, or a combination thereof.

These and other aspects of the invention are set forth in more detail in the description of the invention below.

BRIEF DESCRIPTION OF THE DRAWINGS

FIGS. 1A-1D show cosalane impairs CCR7 driven human and murine chemotaxis. (A, B) Chemotaxis media with or without CCL19 (A) or CCL21 (B) was added to the lower chambers of the chemotaxis device. Previously untreated H9 cells were then placed in the upper chambers of the device with or without cosalane at a concentration of 2 µM. The chamber was then placed at 37° C. for 3.5 hours and total H9 migration from each upper to lower chamber determined. (A) *P=0.048 for comparison between H9 cells/30 nM CCL19 and H9 cells/30 nM CCL19/2 µM cosalane by Student's t test. (B) P>0.05 for comparison between H9 cells/200 nM CCL21 and H9 cells/200 nM CCL21/2 µM cosalane. (C, D) Chemotaxis media with or without CCL19 (C) or CCL21 (D) was added to the lower chambers of the chemotaxis device. Previously untreated primary murine T cells were then placed in the upper chambers of the device with or without cosalane at a concentration of 2 µM. Total T cell migration from each upper to lower chamber was then determined. (C) *P=0.029. (D) *P<0.001.

FIGS. 2A-2D show cosalane pre-treatment alone impairs CCR7 driven human and murine chemotaxis. (A, B) Chemotaxis media with or without CCL19 (A) or CCL21 (B) was added to the lower chambers of the chemotaxis device. H9 cells were incubated with either DMSO vehicle alone or an equal volume of cosalane at a concentration of 10 mcg/ml (13 µM) for one hour at 37° C. The cells were then washed and placed in fresh compound-free media prior to being added to the upper chambers of the chemotaxis apparatus. Total cell migration was then determined as in FIGS. 1A-1D. *P<0.0001 for comparison between H9 cells/30 nM CCL19 and H9 cells/30 nM CCL19/cosalane incubation by Student's t test. (B) *P=0.024. (C, D) Chemotaxis media with or without CCL19 (C) or CCL21 (D) was added to the lower chambers of the chemotaxis device. Primary murine T cells were incubated with either DMSO vehicle alone or an equal volume of cosalane at a concentration of 10 mcg/ml (13 µM). The cells were then washed and placed in fresh compound-free media prior to being added to the upper chambers of the chemotaxis apparatus. (C) *P<0.0001. (D) *P<0.0001.

FIGS. 4A-4D show cosalane does not affect $T_{con}$ proliferation in vitro and does not impair donor lymphoid or myeloid engraftment after HSCT. (A) B6 $T_{cons}$ were purified and incubated with increasing concentrations of cosalane or equal volumes of DMSO vehicle in normal saline for one hour at 37° C. The cells were then washed and cultured on 24 well plates pre-coated with anti-CD3 and anti-CD28 antibody in the presence of supplemental IL-2 for 72 hours. The number of cells per well were then quantified. P>0.05 for all cell number comparisons by the Mann-Whitney test. (B) Irradiated B6D2 recipients were transplanted with $3\times10^6$ eGFP$^+$ B6 TCD BM cells plus $4\times10^6$ eGFP$^+$ B6 $T_{cons}$. The entire donor stem cell product (TCD BM cells plus $T_{cons}$) was incubated with either cosalane (15 µg/ml) or DMSO vehicle prior to transplant. On transplant day +10 total numbers of donor (eGFP$^+$) cells in the spleen were determined by flow cytometry. N=5 mice per treatment group. P>0.05 for all pairwise cell number comparisons between DMSO and cosalane cell recipients by the Mann-Whitney test. (C, D) B6D2 recipients were transplanted as in (B) but followed for survival and scored for aGVHD. N=4 BM only. N=10 for all other treatment groups. (A) *P=0.0006 for survival curve comparison between BM with $T_{cons}$/DMSO and BM with $T_{cons}$/cosalane groups. (B) *P=0.0007 for aGVHD score comparison between BM with $T_{cons}$/DMSO and BM with $T_{cons}$/cosalane groups on day +60.

FIGS. 7A-7E show cosalane attenuates aGVHD in a CCR7 associated manner and alters donor $T_{con}$ trafficking into SLT early after transplant. (A, B) BALB/c mice were lethally irradiated on transplant day −1. On day 0 recipients were administered $5 \times 10^6$ TCD B6 BM cells +/−$3 \times 10^6$ CCR7$^{-/-}$ B6 $T_{cons}$. Donor $T_{cons}$ were incubated ex vivo with DMSO vehicle or cosalane diluted in normal saline at 15 µg/ml. The cells were then mixed with untreated TCD B6 BM cells and administered immediately to recipient mice by tail vein injection. Mice were then followed for survival and scored for aGVHD. N=2 BM only. N=6 for all other treatment groups. (A) P>0.05 for survival curve comparison between BM with CCR7$^{-/-}$ $T_{cons}$/DMSO and BM with CCR7$^{-/-}$ $T_{cons}$/cosalane groups. (B) P>0.05 for aGVHD score comparison between BM with CCR7$^{-/-}$ $T_{cons}$/DMSO and BM with CCR7$^{-/-}$ $T_{cons}$/cosalane groups on day +24. (C, D) BALB/c mice were transplanted as in A, B. Donor CCR7$^{-/-}$ B6 $T_{cons}$, however, were incubated ex vivo with DMSO vehicle or cosalane diluted in normal saline at 30 µg/ml. N=2 BM only. N=9 for all other treatment groups. (C) *P=0.0481 for survival curve comparison between BM with CCR7$^{-/-}$ $T_{cons}$/DMSO and BM with CCR7$^{-/-}$ $T_{cons}$/cosalane groups. (D) P>0.05 for aGVHD score comparison between BM with CCR7$^{-/-}$ $T_{cons}$/DMSO and BM with CCR7$^{-/-}$ $T_{cons}$/cosalane groups on day +67. (E) B6D2 mice were lethally irradiated on transplant day −1. On day 0 recipients were administered $5 \times 10^6$ eGFP$^+$ B6 $T_{cons}$. Donor $T_{cons}$ were incubated ex vivo with DMSO vehicle or cosalane diluted in normal saline at 15 µg/ml. Recipient mice were subsequently killed after 36 hours. Lymphoid organs were subsequently harvested and homogenized. Total eGFP levels were then determined by ELISA. N=6 per treatment group. *P=0.0043 for spleen comparison between DMSO and cosalane groups by Mann-Whitney test. P=0.0022 for ILN comparison. *P=0.0022 for MLN comparison.

DETAILED DESCRIPTION OF THE INVENTION

Figure 3A:
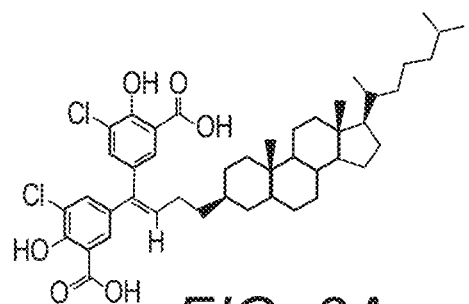
FIGS. 3A-3I show donor $T_{cons}$ exposed to cosalane ex vivo generate attenuated aGVHD responses. (A) The chemical structure of cosalane. (B, C) B6D2 mice were irradiated to 950 rads on transplant day −1. On day 0 recipients were administered $3 \times 10^6$ T cell depleted (TCD) B6 bone marrow (BM) cells +/−$4 \times 10^6$ whole splenic B6 $T_{cons}$ (CD25$^-$ CD4$^+$ and CD25$^-$CD8$^+$ T cells in a 1:1 ratio). Those mice receiving $T_{cons}$ were dosed with cosalane at 10 mg/kg or an equal volume of DMSO vehicle via intravenous injection on day 0 immediately prior to transplant and then again on transplant days +3 and +6. N=2 BM only. N=6 for all other treatment groups. (B) Mice were followed for survival. P>0.05 for survival curve comparison between BM/$T_{cons}$ and BM/$T_{cons}$ with cosalane groups by the log-rank test. (C) Mice were scored for acute GVHD twice weekly using a validated scoring system. Recipients were assigned a score from 0-2 for five separate clinical parameters including weight loss, activity, kyphosis, fur ruffling, and skin breakdown. Individual scores were then added for a total score ranging from 0-10. P>0.05 for aGVHD score comparison between BM/$T_{cons}$ and BM/$T_{cons}$ with cosalane groups on day +40 by the Mann-Whitney test. (D, E) B6D2 mice were lethally irradiated on transplant day −1. On day 0 recipients were administered $3 \times 10^6$ TCD B6 BM cells +/−$4 \times 10^6$ whole B6 $T_{cons}$ Donor $T_{cons}$ were incubated ex vivo with cosalane diluted in normal saline at 10 µg/ml, cosalane diluted in normal saline plus 1% bovine serum albumin at 10 µg/ml, or an equal volume of DMSO in normal saline for one hour at 37° C. The cells were then mixed with untreated TCD B6 BM cells and administered immediately to recipient mice by tail vein injection. Mice were then followed for survival and scored for aGVHD. N=4 BM only, N=8 BM with $T_{cons}$/DMSO, N=8 BM with $T_{cons}$/cosalane in saline, N=4 BM with $T_{cons}$/cosalane with BSA. (D) *P=0044 for survival curve comparison between BM with $T_{cons}$/DMSO and BM with $T_{cons}$/cosalane in saline groups by the log-rank test. P>0.05 for survival curve comparison between BM with $T_{cons}$/DMSO and BM with $T_{cons}$/cosalane with BSA groups. (E) *P=0.026 for aGVHD comparison between BM with $T_{cons}$/DMSO and BM with $T_{cons}$/cosalane in saline on day +601 (F, G) BALB/c mice were irradiated to 800 rads on transplant day −1. On day 0 recipients were administered $5 \times 10^6$ TCD B6 BM cells +/−$5 \times 10^5$ whole B6 $T_{cons}$ incubated ex vivo with cosalane at 15 µg/ml in normal saline alone or an equal volume of DMSO vehicle in saline. Mice were then followed for survival and scored for aGVHD. N=3 BM only. N=10 for all other treatment groups. (F) *P=0.01 for survival curve comparison between BM with $T_{cons}$/DMSO and BM with $T_{cons}$/cosalane groups. (G) P>0.05 for aGVHD score comparison between BM with $T_{cons}$/DMSO and BM with $T_{cons}$/cosalane groups on day +47. (H, I) NSG mice were irradiated to 200 rads on transplant day −1. On day 0 recipients were administered $7 \times 10^6$ human peripheral blood mononuclear cells incubated ex vivo with DMSO or cosalane at 15 mg/ml. Mice were then followed for survival and scored for aGVHD. N=5 in both treatment groups. (H) *P=0.0064 for survival curve comparison. (I) P>0.05 for aGVHD score comparison on day +30.

The present invention will now be described in more detail with reference to the accompanying drawings, in which preferred embodiments of the invention are shown. This invention may, however, be embodied in different forms and should not be construed as limited to the embodiments set forth herein. Rather, these embodiments are provided so that this disclosure will be thorough and complete, and will fully convey the scope of the invention to those skilled in the art.

Unless otherwise defined, all technical and scientific terms used herein have the same meaning as commonly understood by one of skill in the art to which this invention belongs. The terminology used in the description of the invention herein is for the purpose of describing particular embodiments only and is not intended to be limiting of the invention. All publications, patent applications, patents, patent publications and other references cited herein are incorporated by reference in their entireties for the teachings relevant to the sentence and/or paragraph in which the reference is presented.

As used in the description of the invention and the appended claims, the singular forms "a," "an," and "the" are intended to include the plural forms as well, unless the context clearly indicates otherwise.

Also as used herein, "and/or" refers to and encompasses any and all possible combinations of one or more of the associated listed items, as well as the lack of combinations when interpreted in the alternative ("or").

The term "about," as used herein when referring to a measurable value such as an amount of polypeptide, dose, time, temperature, enzymatic activity or other biological activity and the like, is meant to encompass variations of ±10%, ±5%, ±1%, ±0.5%, or even ±0.1% of the specified amount.

The transitional phrase "consisting essentially of" means that the scope of a claim is to be interpreted to encompass the specified materials or steps recited in the claim, and those that do not materially affect the basic and novel characteristics of the claimed invention.

The term "modulate," "modulates," or "modulation" refers to enhancement (e.g., an increase) or inhibition (e.g., a decrease) in the specified level or activity.

The term "enhance" or "increase" refers to an increase in the specified parameter of at least about 1.25-fold, 1.5-fold, 2-fold, 3-fold, 4-fold, 5-fold, 6-fold, 8-fold, 10-fold, twelve-fold, or even fifteen-fold.

The term "inhibit" or "reduce" or grammatical variations thereof as used herein refers to a decrease or diminishment in the specified level or activity of at least about 15%, 25%, 35%, 40%, 50%, 60%, 75%, 80%, 90%, 95% or more. In particular embodiments, the inhibition or reduction results in little or essentially no detectable activity (at most, an insignificant amount, e.g., less than about 10% or even 5%).

A "therapeutically effective" amount as used herein is an amount that provides some improvement or benefit to the subject. Alternatively stated, a "therapeutically effective" amount is an amount that will provide some alleviation, mitigation, or decrease in at least one clinical symptom in the subject. Those skilled in the art will appreciate that the therapeutic effects need not be complete or curative, as long as some benefit is provided to the subject.

By the terms "treat," "treating," or "treatment of," it is intended that the severity of the subject's condition is reduced or at least partially improved or modified and that some alleviation, mitigation or decrease in at least one clinical symptom is achieved.

A "prevention effective" amount as used herein is an amount that is sufficient to prevent (as defined herein) the disease, disorder and/or clinical symptom in the subject. Those skilled in the art will appreciate that the level of prevention need not be complete, as long as some benefit is provided to the subject.

The terms "prevent," "preventing," and "prevention" (and grammatical variations thereof) refer to a decrease and/or delay in the extent or severity of a disease, disorder and/or clinical symptom(s) after onset relative to what would occur in the absence of carrying out the methods of the invention prior to the onset of the disease, disorder and/or clinical symptom(s).

"Concurrently" means sufficiently close in time to produce a combined effect (that is, concurrently can be simultaneously, or it can be two or more events occurring within a short time period before or after each other). In some embodiments, the administration of two or more compounds "concurrently" means that the two compounds are administered closely enough in time that the presence of one alters the biological effects of the other. The two compounds can be administered in the same or different formulations or sequentially. Concurrent administration can be carried out by mixing the compounds prior to administration, or by administering the compounds in two different formulations, for example, at the same point in time but at different anatomic sites or using different routes of administration.

A "synergistic" effect, as used herein, is an effect that is greater than additive when two molecules are administered to a subject simultaneously or sequentially.

The term "decreasing the risk of developing graft versus host disease" refers to a decrease in the likelihood that a subject undergoing a HSC transplant will develop GVHD and/or an increase in the likelihood that a subject will develop less severe GVHD than if the method of the present invention was not carried out. The severity may be quantitated for comparison purposes by any method known in the art. One example of a quantitation method is to grade the GVHD from a low of 1 to a high of 4 as is known by clinicians, e.g., using the Glucksberg grade or the International Bone Marrow Transplant Registry grading system. Another example, e.g., for use with laboratory animals, is to assign a score for different GVHD symptoms, such as weight loss, activity, fur ruffling, kyphosis, and skin lesions, and then totaling the score for each subject.

The term "decreasing the risk of microbial infection" refers to a decrease in the likelihood that a subject undergoing a HSC transplant will develop an infection and/or an increase in the likelihood that a subject will develop a less severe infection than if the method of the present invention was not carried out.

One aspect of the invention relates to a method for modifying HSC to decrease the risk of developing graft versus host disease following transplantation of the cells into a subject, comprising contacting the HSC with an effective amount of a compound of Formula I or Formula II or a pharmaceutically acceptable salt thereof:

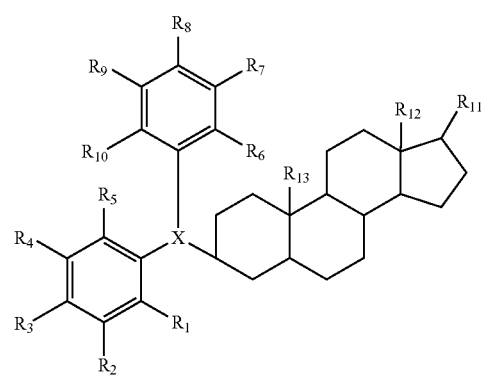

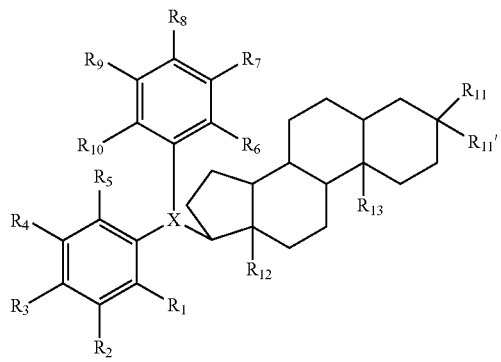

II

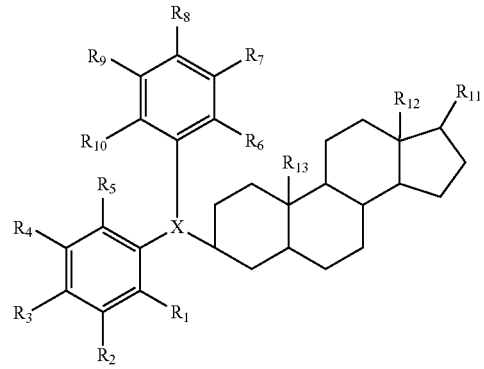

I

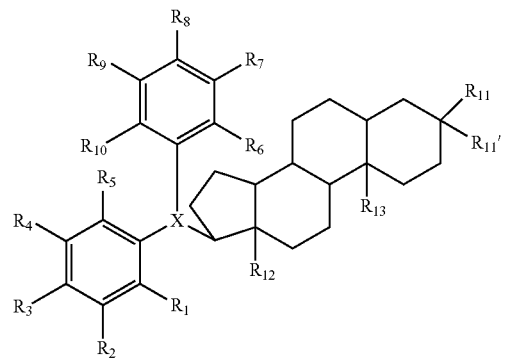

II wherein
$R_1$ to $R_{11}$ and $R_{11'}$ are independently H, halogen, hydroxy, amino, $C_1$-$C_5$ alkoxy, benzoyloxy, $R_{14}C(O)O$, COOH or a salt thereof, $SO_3H$ or a salt thereof, $PO_3H_2$ or a salt thereof, $C_1$-$C_{24}$ alkyl, $COOR_{15}$, $SO_3R_{16}$, $C(O)NR_{17}R_{18}$, $SO_2NR_{19}R_{20}$, $SR_{21}$, $SCH_2R_{25}$, $SC(O)R_{21}$, $NR_{22}R_{23}$, NHC(O)—$R_{24}$, $O(CH_2)_n$—$R_{26}$—$R_{27}$, $OC(O)N(H)C(H)(R_{28})COOR_{29}$;

$R_{12}$ and $R_{13}$ are $C_1$-$C_7$ alkyl groups;

$R_{14}$ is H or $C_1$-$C_5$ alkyl;

$R_{15}$ is aryl or $C_1$-$C_5$ alkyl;

$R_{16}$ is aryl or $C_1$-$C_5$ alkyl;

$R_{17}$ and $R_{18}$ are each independently H, $C_1$-$C_5$ alkyl, aryl or hydroxy;

$R_{19}$ and $R_{20}$ are each independently H, $C_1$-$C_5$ alkyl or aryl;

$R_{21}$ is $C_1$-$C_5$ alkyl or aryl;

$R_{22}$ and $R_{23}$ are each independently H, $C_1$-$C_5$ alkyl or aryl;

$R_{24}$ is aryl optionally substituted with COOH or a salt thereof, or $C_1$-$C_7$ alkoxy;

$R_{25}$ is aryl;

$R_{26}$ is aryl;

$R_{27}$ is COOH or a salt thereof, $B(OH)_2$ or a salt thereof, nitro, $C_1$-$C_7$ alkoxy or aryl, wherein the aryl is substituted with COOH or a salt thereof, $B(OH)_2$ or a salt thereof, nitro or $C_1$-$C_7$ alkoxy;

$R_{28}$ is an amino acid side chain;

$R_{29}$ is H or a $C_1$-$C_4$ alkyl;

X is a ($C_1$-$C_7$ alkylene) or ($C_1$-$C_7$ alkylene)C(O)NH; and n is 1 to 7;

thereby decreasing the risk of developing graft versus host disease following transplantation of the cells.

Another aspect of the invention relates to a method for decreasing the risk of developing graft versus host disease following transplantation of a graft comprising HSC in a subject in need thereof, comprising contacting the graft with an effective amount of a compound of Formula I or Formula II or a pharmaceutically acceptable salt thereof:

wherein
$R_1$ to $R_{11}$ and $R_{11'}$ are independently H, halogen, hydroxy, amino, $C_1$-$C_5$ alkoxy, benzoyloxy, $R_{14}C(O)O$, COOH or a salt thereof, $SO_3H$ or a salt thereof, $PO_3H_2$ or a salt thereof, $C_1$-$C_{24}$ alkyl, $COOR_{15}$, $SO_3R_{16}$, $C(O)NR_{17}R_{18}$, $SO_2NR_{19}R_{20}$, $SR_{21}$, $SCH_2R_{25}$, $SC(O)R_{21}$, $NR_{22}R_{23}$, NHC(O)—$R_{24}$, $O(CH_2)_n$—$R_{26}$—$R_{27}$, $OC(O)N(H)C(H)(R_{28})COOR_{29}$;

$R_{12}$ and $R_{13}$ are $C_1$-$C_7$ alkyl groups;

$R_{14}$ is H or $C_1$-$C_5$ alkyl;

$R_{15}$ is aryl or $C_1$-$C_5$ alkyl;

$R_{16}$ is aryl or $C_1$-$C_5$ alkyl;

$R_{17}$ and $R_{18}$ are each independently H, $C_1$-$C_5$ alkyl, aryl or hydroxy;

$R_{19}$ and $R_{20}$ are each independently H, $C_1$-$C_5$ alkyl or aryl;

$R_{21}$ is $C_1$-$C_5$ alkyl or aryl;

$R_{22}$ and $R_{23}$ are each independently H, $C_1$-$C_5$ alkyl or aryl;

$R_{24}$ is aryl optionally substituted with COOH or a salt thereof, or $C_1$-$C_7$ alkoxy;

$R_{25}$ is aryl;

$R_{26}$ is aryl;

$R_{27}$ is COOH or a salt thereof, $B(OH)_2$ or a salt thereof, nitro, $C_1$-$C_7$ alkoxy or aryl, wherein the aryl is substituted with COOH or a salt thereof, $B(OH)_2$ or a salt thereof, nitro or $C_1$-$C_7$ alkoxy;

$R_{28}$ is an amino acid side chain;

$R_{29}$ is H or a $C_1$-$C_4$ alkyl;

X is a ($C_1$-$C_7$ alkylene) or ($C_1$-$C_7$ alkylene)C(O)NH; and n is 1 to 7; and transplanting the contacted graft into the subject;

thereby decreasing the developing risk of graft versus host disease.

In some embodiments of the compound of Formula I or Formula II, $R_1$, $R_5$, $R_6$ and $R_{10}$ are H, $R_2$ and $R_7$ are chlorine, $R_{11}$ is $CH(CH_3)(CH_2)_3 CH(CH_3)_2$, $R_{12}$ and $R_{13}$ are methyl and X is C=CH(CH$_2$)$_2$. In certain embodiments, R$_3$ and R$_8$ are O(CH$_2$)$_n$—R$_{26}$—R$_{27}$, wherein n is 1, R$_{26}$ is phenyl, R$_{27}$ is selected from the group consisting of aryl, nitro, COOH or a salt thereof, B(OH)$_2$ or a salt thereof, C$_1$-C$_7$ alkoxy and combinations thereof, wherein the aryl of R$_{27}$ may be substituted with nitro, COOH or salt thereof, B(OH)$_2$ or a salt thereof, C$_1$-C$_7$ alkoxy and combinations thereof.

In some embodiments of the compound of Formula I or Formula II, R$_1$, R$_5$, R$_6$, R$_{10}$, R$_{11}$ and R$_{11'}$ are H, R$_2$ and R$_7$ are chlorine, R$_{12}$ and R$_{13}$ are methyl and X is C=CH(CH$_2$)$_2$. In certain embodiments, R$_3$ and R$_8$ are hydroxy, and R$_4$ and R$_9$ are OC(O)N(H)C(H)(R$_{28}$)COOH, wherein R$_{28}$ is H, CH$_2$(CH)$_2$CH$_3$, CH$_2$Ph, CH$_2$COOH or a salt thereof, or CH$_2$CH$_2$COOH or a salt thereof.

In some embodiments, the compound of Formula I or Formula II is cosalane or a pharmaceutically acceptable salt or prodrug thereof

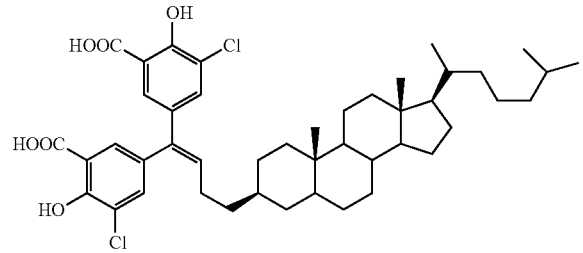 [SMILES: CC(C)CCCC(C)[C@H]1CCC2C3CCC4C[C@@H](CCC=C(c5cc(Cl)c(O)c(C(=O)O)c5)c5cc(Cl)c(O)c(C(=O)O)c5)CC[C@]4(C)C3CC[C@@]21C]

In some embodiments, the compound of Formula I or Formula II is not cosalane.

One important advantage of the methods of the present invention is the ability to attenuate GVHD while substantially maintaining the anti-cancer activity of the graft, e.g., a graft-versus leukemia effect.

The GVHD may be any type of GVHD. In some embodiments, the GVHD is acute GVHD, e.g., cases presenting within 100 days of transplantation (classic acute GVHD) or after 100 days (late onset acute GVHD) and having the features of acute GVHD (such as maculopapular rash, persistent nausea and/or emesis, abdominal cramps with diarrhea, rising serum bilirubin concentration). In some embodiments, the GVHD is chronic GVHD, e.g., having the features of chronic GVHD (such as skin involvement resembling lichen planus or scleroderma, dry oral mucosa with ulcerations and sclerosis of the gastrointestinal tract) and no features of acute GVHD, or overlap syndrome (acute on chronic GVHD).

The graft may be any tissue sample that comprises HSC. The graft may comprise other cell types in addition to HSC, such as T cells and other white blood cells, red blood cells, etc. In certain embodiments, the graft is from bone marrow of a donor. In certain embodiments, the graft is from peripheral blood of a donor.

The donor may be any subject that has suitable tissue for donation. In some embodiments, the donor is allogeneic with the recipient subject. In certain embodiments, the donor and the recipient are human. In certain embodiments, the donor and the recipient are laboratory animals. In some embodiments, the donor is xenogeneic with the recipient subject, e.g., in laboratory studies wherein human cells are transplanted in a mouse.

In particular embodiments, the methods of the invention are carried out ex vivo, e.g., wherein the graft is isolated from the donor prior to contact with the compound of Formula I or Formula II and the isolated graft in a suitable medium is contacted with the compound of Formula I or Formula II. An important advantage of the present invention is the ability to modify HSC ex vivo by contacting them with a compound of Formula I or Formula II and then delivering the modified HSC to a subject without any need for further contact with the compound.

In some embodiments, the graft material may be isolated from the donor and then contacted as is with the compound of Formula I or Formula II. In some embodiments, the graft may be separated into individual cell components prior to being contacted with the compound of Formula I or Formula II. For example, HSC or T cells may be separated from the graft material. In certain embodiments, only certain cell components are contacted with the compound of Formula I or Formula II, e.g., only the T cells. Some or all of the separated cell components may be combined together before or after being contacted with the compound of Formula I or Formula II.

The ex vivo contacting step may be carried out in any suitable medium that can support the health of the graft. An example of a suitable medium is saline. In some embodiments, the medium contains substantially no soluble protein, such as albumin. The medium may contain less than about 1%, 0.5%, 0.1%, 0.05%, 0.01%, 0.005%, or 0.001% by weight soluble protein.

The ex vivo contacting step may be carried out for any length of time that achieves the desired modification of the HSC. Suitable times may be, for example, about 15, 30, 45, 60, 75, 90, 105, 120, 135, 150, 165, or 180 minutes or more, e.g., about 30 to 90 minutes, e.g., about 60 minutes.

The ex vivo contacting step may be carried out at any temperature that is suitable for culturing cells, e.g., about 30-42° C., e.g., about 37° C.

The amount or concentration of the compound of Formula I or Formula II that is used to contact the graft may be any suitable amount or concentration and can be readily determined by one of skill in the art for each compound of the invention. In embodiments wherein the compound is cosalane, the concentration may be about 1 to about 50 µg/ml, e.g., about 10 to about 30 µg/ml, e.g., about 1, 5, 10, 15, 20, 25, 30, 35, 40, 45, or 50 µg/ml or any range therein.

In other embodiments, the methods of the invention are carried out in vivo, e.g., wherein the graft is transplanted in a subject and the compound of Formula I or Formula II is delivered to the subject in order to contact the transplanted graft. The compound may be delivered to the subject by any suitable route of administration, e.g., systemically, such as orally or intravenously, or locally, e.g., at the site of the transplant.

The compound may be delivered to the subject prior to the transplant, concurrently with the transplant, and/or after the transplant. For example, the compound may be delivered 0.5, 1, 2, 3, 4, 5, 6, 9, 12, 24, 48, or 72 hours before and/or after the transplant procedure. The delivery may be continuous or repeated, e.g., every 6, 12, 18, 24, 48, or 72 hours.

In certain embodiments, the methods may comprise both ex vivo and in vivo steps, e.g., the graft may be isolated from the donor and contacted with the compound of Formula I or Formula II, transplanted into the subject, and then additional compound delivered to the subject. In some embodiments, the compound used in the ex vivo step may be the same as or different from the compound used in the in vivo step.

A further aspect of the invention relates to a method for decreasing the risk of microbial infection after transplantation of a graft comprising hematopoietic stem cells in a subject in need thereof, comprising administering to the subject an effective amount of a compound of Formula I or Formula II or a pharmaceutically acceptable salt thereof:

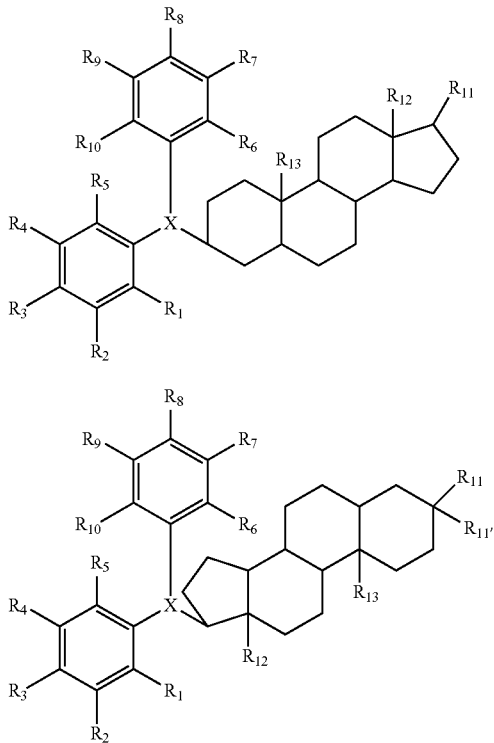

wherein
- $R_1$ to $R_{11}$ and $R_{11'}$ are independently H, halogen, hydroxy, amino, $C_1$-$C_5$ alkoxy, benzoyloxy, $R_{14}C(O)O$, COOH or a salt thereof, $SO_3H$ or a salt thereof, $PO_3H_2$ or a salt thereof, $C_1$-$C_{24}$ alkyl, $COOR_{15}$, $SO_3R_{16}$, $C(O)NR_{17}R_{18}$, $SO_2NR_{19}R_{20}$, $SR_{21}$, $SCH_2R_{25}$, $SC(O)R_{21}$, $NR_{22}R_{23}$, NHC(O)—$R_{24}$, $O(CH_2)_n$—$R_{26}$—$R_{27}$, $OC(O)N(H)C(H)(R_{28})COOR_{29}$;
- $R_{12}$ and $R_{13}$ are $C_1$-$C_7$ alkyl groups;
- $R_{14}$ is H or $C_1$-$C_5$ alkyl;
- $R_{15}$ is aryl or $C_1$-$C_5$ alkyl;
- $R_{16}$ is aryl or $C_1$-$C_5$ alkyl;
- $R_{17}$ and $R_{18}$ are each independently H, $C_1$-$C_5$ alkyl, aryl or hydroxy;
- $R_{19}$ and $R_{20}$ are each independently H, $C_1$-$C_5$ alkyl or aryl;
- $R_{21}$ is $C_1$-$C_5$ alkyl or aryl;
- $R_{22}$ and $R_{23}$ are each independently H, $C_1$-$C_5$ alkyl or aryl;
- $R_{24}$ is aryl optionally substituted with COOH or a salt thereof, or $C_1$-$C_7$ alkoxy;
- $R_{25}$ is aryl;
- $R_{26}$ is aryl;
- $R_{27}$ is COOH or a salt thereof, $B(OH)_2$ or a salt thereof, nitro, $C_1$-$C_7$ alkoxy or aryl, wherein the aryl is substituted with COOH or a salt thereof, $B(OH)_2$ or a salt thereof, nitro or $C_1$-$C_7$ alkoxy;
- $R_{28}$ is an amino acid side chain;
- $R_{29}$ is H or a $C_1$-$C_4$ alkyl;
- X is a ($C_1$-$C_7$ alkylene) or ($C_1$-$C_7$ alkylene)C(O)NH; and n is 1 to 7;

thereby decreasing the risk of microbial infection.

The compound of Formula I or Formula II may be any compound described above.

In one embodiment, the compound is cosalane. In one embodiment, the compound is not cosalane. On advantage of the present invention is the combined effect from a single compound of decreasing the risk of developing GVHD coupled with the anti-viral activity of the compound to decrease the risk of opportunistic infection.

The graft may be any graft comprising HSC from any suitable donor as described above.

In some embodiments, the method is an in vivo method, e.g., wherein the graft is transplanted in a subject and the compound of Formula I or Formula II is delivered to the subject. The compound may be delivered to the subject by any suitable route of administration, e.g., systemically, such as orally or intravenously, or locally, e.g., at the site of the transplant.

The compound may be delivered to the subject prior to the transplant, concurrently with the transplant, and/or after the transplant. For example, the compound may be delivered 0.5, 1, 2, 3, 4, 5, 6, 9, 12, 24, 48, or 72 hours before and/or after the transplant procedure. The delivery may be continuous or repeated, e.g., every 6, 12, 18, 24, 48 or 72 hours.

In some embodiments, the method is an ex vivo method, e.g., wherein the graft is isolated prior to contact with the compound of Formula I or Formula II and the isolated graft in a suitable medium is contacted with the compound of Formula I or Formula II.

In certain embodiments, the methods may comprise both ex vivo and in vivo steps, e.g., the graft may be isolated and contacted with the compound of Formula I or Formula II, transplanted into the subject, and then additional compound delivered to the subject. In some embodiments, the compound used in the ex vivo step may be the same as or different from the compound used in the in vivo step.

The microbial infection may be any type of infection to which a transplantation subject is susceptible. The microbial infection may be a viral infection (e.g., cytomegalovirus, herpes simplex virus, Epstein Barr virus, respiratory syncytial virus, influenza virus), a bacterial infection, and/or a fungal infection (e.g., aspergillus).

With respect to the compounds of Formula I or Formula II, the term "alkyl" means an aliphatic hydrocarbon which may either be straight chain or branched, and includes, for example, methyl, ethyl, and structural isomers of propyl, butyl, pentyl, hexyl, heptyl, and octyl. The term "alkylene" as used herein refers to a saturated or unsaturated hydrocarbon which may be straight chain or branched, and including, for example, methylene, ethylene, and structural isomers of propylene, butylene, pentylene, hexylene, heptylene and octylene. The term "aryl" as used herein refers to a group whose molecules have the ring structure characteristic of, for example, benzene, naphthalene, anthracene and fluorene. For example, an aryl group includes phenyl, naphthyl, anthracyl, phenanthryl, fluorenyl and biphenyl.

The halogen group may be selected from halogens known in the art, especially chlorine and bromine. It is further noted that where substituents are indicated, one or more of the indicated substituents may be present.

In certain embodiments of the invention, the compound may be cosalane, wherein $R_1$, $R_5$, $R_6$, and $R_{10}$ are H, $R_2$ and $R_7$ are chlorine, $R_3$ and $R_8$ are hydroxy, $R_4$ and $R_9$ are COOH or a salt thereof, $R_{11}$ is $CH(CH_3)(CH_2)_3CH(CH_3)_2$, $R_{12}$ and $R_{13}$ are methyl, X is $C=CH(CH_2)_2$, wherein cosalane has the following structure:

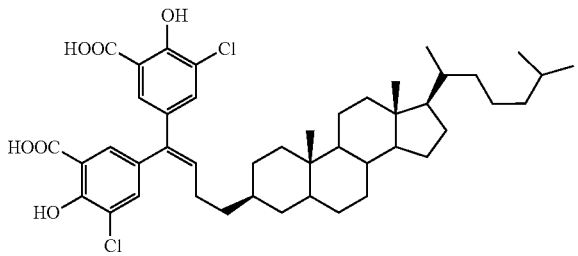 [SMILES: CC(C)CCCC(C)[C@H]1CCC2C3CCC4C[C@@H](CCC=C(c5cc(Cl)c(O)c(C(=O)O)c5)c5cc(Cl)c(O)c(C(=O)O)c5)CC[C@]4(C)C3CC[C@@]21C]

In other embodiments of the invention, the hydroxyl group of $R_3$ and/or $R_8$ of cosalane may be replaced with $OCH_2$—$R_{26}R_{27}$, wherein $R_{26}$ is an aryl group, such as a phenyl (Ph) group, and $R_{27}$ may be COOH or a salt thereof. When the aryl group of $R_{26}$ is phenyl, carboxybenzyl analogs of cosalane are formed that may be advantageously utilized in the methods described herein. The phenyl ring of carboxybenzyl may be substituted with the carboxyl group at any available ring position, including the ortho, meta, or para positions, although ortho and meta positions are preferred. Alternatively, a substituent on the phenyl ring may be nitro ($NO_2$), to form nitrobenzyl derivatives of cosalane or may be $B(OH)_2$ to form boronic acid derivatives of cosalane. The nitro and $B(OH)_2$ groups may also be present at any available ring position, but preferably at the meta position. Furthermore, a substituent on the phenyl ring may be another phenyl ring, preferably at the para position, wherein the phenyl ring substituent may be substituted by COOH or a salt thereof, $B(OH)_2$ or a salt thereof, nitro or a $C_1$-$C_7$ alkoxy group, preferably a methoxy group.

Yet other compounds that may advantageously be utilized in the methods of the present invention include compounds of Formula I, wherein $R_1$ to $R_{11}$ are independently H, a halogen, hydroxy, amino, $C_1$-$C_5$ alkoxy, benzoyloxy, $R_{14}C(O)O$, wherein $R_{14}$ is H or $C_1$-$C_5$ alkyl; COOH or a salt thereof, $SO_3H$ or a salt thereof, $PO_3H_2$ or a salt thereof, $C_1$-$C_{24}$ alkyl, $COOR_{15}$ wherein $R_{15}$ is aryl or $C_1$-$C_5$ alkyl; $SO_3R_{16}$, wherein $R_{16}$ is aryl or $C_1$-$C_5$ alkyl; $C(O)NR_{17}R_{18}$ wherein $R_{17}$ and $R_{18}$ are each independently H, $C_1$-$C_5$ alkyl, aryl or hydroxy; $SO_2NR_{19}R_{20}$ wherein $R_{19}$ and $R_{20}$ are each independently H, $C_1$-$C_5$ alkyl or aryl; $SR_{21}$ wherein $R_{21}$ is $C_1$-$C_5$ alkyl or aryl; $SCH_2R_{25}$, wherein $R_{25}$ is aryl; $SC(O)R_{21}$ wherein $R_{21}$ is as defined above; $NR_{22}R_{23}$ wherein $R_{22}$ and $R_{23}$ are each independently H, $C_1$-$C_5$ alkyl or aryl; $NHC(O)$—$R_{24}$, wherein $R_{24}$ is aryl optionally substituted with COOH or a salt thereof, or $C_1$-$C_7$ alkoxy; $O(CH_2)_n$—$R_{26}$—$R_{27}$, wherein n is 1 to 7, $R_{26}$ is aryl, $R_{27}$ is COOH or a salt thereof, $B(OH)_2$ or a salt thereof, nitro, $C_1$-$C_7$ alkoxy or aryl wherein the aryl of $R_{27}$ is substituted with COOH or a salt thereof, $B(OH)_2$ or a salt thereof, nitro or $C_1$-$C_7$ alkoxy; $OC(O)N(H)C(H)(R_{28})COOR_{29}$, wherein $R_{28}$ is an amino acid side chain and $R_{29}$ is H or a $C_1$-$C_4$ alkyl; wherein at least one of $R_3$ or $R_8$ is $O(CH_2)_n$—$R_{26}$—$R_{27}$, wherein n is 1 to 7, $R_{26}$ is aryl, $R_{27}$ is $B(OH)_2$ or a salt thereof, nitro, $C_1$-$C_7$ alkoxy, or aryl, wherein the aryl of $R_{27}$ is substituted with COOH or a salt thereof, $B(OH)_2$ or a salt thereof, nitro or $C_1$-$C_7$ alkoxy;

$R_{12}$ and $R_{13}$ are $C_1$-$C_7$ alkyl; and

X is a ($C_1$-$C_7$ alkylene) or ($C_1$-$C_7$ alkylene)$C(O)NH$;

or a pharmaceutically acceptable salt thereof.

In some embodiments of the invention, $R_1$, $R_5$, $R_6$, and $R_{10}$ are H, $R_2$ and/or $R_7$ are halogen, such as chlorine or bromine, $R_3$ and/or $R_8$ are $O(CH_2)_nR_{26}$—$R_{27}$, wherein n is 1 to 7, $R_{26}$ is a phenyl ring substituted with $R_{27}$, which may be COOH or a salt thereof, $B(OH)_2$ or a salt thereof, nitro, or a $C_1$-$C_7$ alkoxy. The phenyl ring may further be substituted with another phenyl ring wherein the phenyl ring substituent may be substituted with COOH or a salt thereof, $B(OH)_2$ or a salt thereof, nitro, or a $C_1$-$C_7$ alkoxy.

In yet other embodiments of the invention, amino acid derivatives of cosalane may be advantageously utilized in the present invention wherein the carboxyl group of $R_4$ and/or $R_9$ of cosalane is conjugated to amino acids, such that at least one of $R_4$ or $R_9$ is $C(O)N(H)C(H)(R_{28})COOR_{29}$, wherein $R_{28}$ is an amino acid side chain and $R_{29}$ is H or a $C_1$-$C_4$ alkyl, and wherein all other R groups are as defined for cosalane. $R_{28}$ may include a wide variety of amino acid side chains, such as the 20 naturally occurring amino acid side chains known to the art, including leucine, glycine, aspartic acid, glutamic acid and alanine. The compounds may have the structure of compound I, wherein $R_1$ to $R_{11}$ are independently H, a halogen, hydroxy, amino, $C_1$-$C_5$ alkoxy, benzoyloxy, $R_{14}C(O)O$, wherein $R_{14}$ is H or $C_1$-$C_5$ alkyl; COOH or a salt thereof, $SO_3H$ or a salt thereof, $PO_3H_2$ or a salt thereof, $C_1$-$C_{24}$ alkyl, $COOR_{15}$ wherein $R_{15}$ is aryl or $C_1$-$C_5$ alkyl; $SO_3R_{16}$, wherein $R_{16}$ is aryl or $C_1$-$C_5$ alkyl; $C(O)NR_{17}R_{18}$ wherein $R_{17}$ and $R_{18}$ are each independently H, $C_1$-$C_5$ alkyl, aryl or hydroxy; $SO_2NR_{19}R_{20}$ wherein $R_{19}$ and $R_{20}$ are each independently H, $C_1$-$C_5$ alkyl or aryl; $SR_{21}$ wherein $R_{21}$ is $C_1$-$C_5$ alkyl or aryl; $SCH_2R_{25}$, wherein $R_{25}$ is aryl; $SC(O)R_{21}$ wherein $R_{21}$ is as defined above; $NR_{22}R_{23}$ wherein $R_{22}$ and $R_{23}$ are each independently H, $C_1$-$C_5$ alkyl or aryl; $NHC(O)$—$R_{24}$, wherein $R_{24}$ is aryl optionally substituted with COOH or a salt thereof, or $C_1$-$C_7$ alkoxy; $O(CH_2)_n$—$R_{26}$—$R_{27}$, wherein n is 1 to 7, $R_{26}$ is aryl, $R_{27}$ is COOH or a salt thereof, $B(OH)_2$ or a salt thereof, nitro, $C_1$-$C_7$ alkoxy or aryl wherein the aryl of $R_{27}$ is substituted with COOH or a salt thereof, $B(OH)_2$ or a salt thereof, nitro or $C_1$-$C_7$ alkoxy; $OC(O)N(H)C(H)(R_{28})COOR_{29}$, wherein $R_{28}$ is an amino acid side chain and $R_{29}$ is H or a $C_1$-$C_4$ alkyl;

wherein at least one of $R_3$ or $R_8$ is $O(CH_2)_n$—$R_{26}$—$R_{27}$, wherein n is 1 to 7, $R_{26}$ is aryl, $R_{27}$ is $B(OH)_2$ or a salt thereof, nitro, $C_1$-$C_7$ alkoxy, or aryl, wherein the aryl of $R_{27}$ is substituted with COOH or a salt thereof, $B(OH)_2$ or a salt thereof, nitro or $C_1$-$C_7$ alkoxy;

wherein at least one of $R_4$ and $R_9$ is $OC(O)N(H)C(H)(R_{28})COOR_{29}$, wherein $R_{28}$ is an amino acid side chain and $R_{29}$ is H or a $C_1$-$C_4$ alkyl radical;

$R_{12}$ and $R_{13}$ are $C_1$-$C_7$ alkyl; and

X is a ($C_1$-$C_7$ alkylene) or ($C_1$-$C_7$ alkylene)$C(O)NH$;

or a pharmaceutically acceptable salt thereof.

Other compounds useful in the methods of the present invention include those having the structure of Formula II, wherein $R_1$ to $R_{11}$ and $R_{11'}$ are independently H, a halogen, hydroxy, amino, $C_1$-$C_5$ alkoxy, benzoyloxy, $R_{14}C(O)O$, wherein $R_{14}$ is H or $C_1$-$C_5$ alkyl; COOH or a salt thereof, $SO_3H$ or a salt thereof, $PO_3H_2$ or a salt thereof, $C_1$-$C_{24}$ alkyl, $COOR_{15}$ wherein $R_{15}$ is aryl or $C_1$-$C_5$ alkyl; $SO_3R_{16}$, wherein $R_{16}$ is aryl or $C_1$-$C_5$ alkyl; $C(O)NR_{17}R_{18}$ wherein $R_{17}$ and $R_{18}$ are each independently H, $C_1$-$C_5$ alkyl, aryl or hydroxy; $SO_2NR_{19}R_{20}$ wherein $R_{19}$ and $R_{20}$ are each independently H, $C_1$-$C_5$ alkyl or aryl; $SR_{21}$ wherein $R_{21}$ is $C_1$-$C_5$ alkyl or aryl; $SCH_2R_{25}$, wherein $R_{25}$ is aryl; $SC(O)R_{21}$ wherein $R_{21}$ is as defined above; $NR_{22}R_{23}$ wherein $R_{22}$ and $R_{23}$ are each independently H, $C_1$-$C_5$ alkyl or aryl; $NHC(O)$—$R_{24}$, wherein $R_{24}$ is aryl optionally substituted with COOH or a salt thereof, or $C_1$-$C_7$ alkoxy; $O(CH_2)_n$—$R_{26}$—$R_{27}$, wherein n is 1 to 7, $R_{26}$ is aryl, $R_{27}$ is COOH or a salt thereof, $B(OH)_2$ or a salt thereof, nitro, $C_1$-$C_7$ alkoxy or aryl, wherein the aryl of $R_{27}$ is substituted with COOH or a salt thereof, $B(OH)_2$ or a salt thereof, nitro or $C_1$-$C_7$ alkoxy; OC(O)N(H)C(H)($R_{28}$)COOR$_{29}$, wherein $R_{28}$ is an amino acid side chain and $R_{29}$ is H or a $C_1$-$C_4$ alkyl;

$R_{12}$ and $R_{13}$ are $C_1$-$C_7$ alkyl; and

X is a ($C_1$-$C_7$ alkylene) or ($C_1$-$C_7$ alkylene)C(O)NH;

or a pharmaceutically acceptable salt thereof.

In one embodiment of the invention, $R_1$, $R_5$, $R_6$, and $R_{10}$ are hydrogen, $R_2$ and $R_7$ are a halogen such as chlorine or bromine, $R_3$ and $R_8$ are hydroxy, $R_4$ and $R_9$ are COOH or a salt thereof, $R_{12}$ and $R_{13}$ are methyl, X is C=CH(CH$_2$)$_2$ and $R_{11}$ and $R_{11'}$ are independently hydrogen or a halogen.

Other compounds useful in the methods of the present invention are those having Formula II, wherein $R_1$ to $R_{11}$ and $R_{11'}$ are independently H, a halogen, hydroxy, amino, $C_1$-$C_5$ alkoxy, benzoyloxy, $R_{14}$C(O)O, wherein $R_{14}$ is H or $C_1$-$C_5$ alkyl; COOH or a salt thereof, SO$_3$H or a salt thereof, PO$_3$H$_2$ or a salt thereof, $C_1$-$C_{24}$ alkyl, COOR$_{15}$ wherein $R_{15}$ is aryl or $C_1$-$C_5$ alkyl; SO$_3$R$_{16}$, wherein $R_{16}$ is aryl or $C_1$-$C_5$ alkyl; C(O)NR$_{17}$R$_{18}$ wherein $R_{17}$ and $R_{18}$ are each independently H, $C_1$-$C_5$ alkyl, aryl or hydroxy; SO$_2$NR$_{19}$R$_{20}$ wherein $R_{19}$ and $R_{20}$ are each independently H, $C_1$-$C_5$ alkyl or aryl; SR$_{21}$ wherein $R_{21}$ is $C_1$-$C_5$ alkyl or aryl; SCH$_2$R$_{25}$, wherein $R_{25}$ is aryl; SC(O)R$_{21}$ wherein $R_{21}$ is as defined above; NR$_{22}$R$_{23}$ wherein $R_{22}$ and $R_{23}$ are each independently H, $C_1$-$C_5$ alkyl or aryl; NHC(O)—$R_{24}$, wherein $R_{24}$ is aryl optionally substituted with COOH or a salt thereof, or $C_1$-$C_7$ alkoxy; O(CH$_2$)$_n$—$R_{26}$—$R_{27}$, wherein n is 1 to 7, $R_{26}$ is aryl, $R_{27}$ is COOH or a salt thereof, $B(OH)_2$ or a salt thereof, nitro, $C_1$-$C_7$ alkoxy or aryl, wherein the aryl of $R_{27}$ is substituted with COOH or a salt thereof, $B(OH)_2$ or a salt thereof, nitro or $C_1$-$C_7$ alkoxy; OC(O)N(H)C(H)($R_{28}$)COOR$_{29}$, wherein $R_{28}$ is an amino acid side chain and $R_{29}$ is H or a $C_1$-$C_4$ alkyl;

wherein at least one of $R_3$ or $R_8$ is O(CH$_2$)$_n$—$R_{26}$—$R_{27}$, wherein n is 1 to 7, $R_{26}$ is aryl, $R_{27}$ is B(OH)$_2$ or a salt thereof, nitro, $C_1$-$C_7$ alkoxy, or aryl wherein the aryl of $R_{27}$ is substituted with COOH or a salt thereof, B(OH)$_2$ or a salt thereof, nitro, or $C_1$-$C_7$ alkoxy;

$R_{12}$ and $R_{13}$ are $C_1$-$C_7$ alkyl; and

X is a ($C_1$-$C_7$ alkylene) or ($C_1$-$C_7$ alkylene)C(O)NH;

or a pharmaceutically acceptable salt thereof.

Other compounds useful in the methods of the present invention are those having the Formula II, wherein $R_1$ to $R_{11}$ and $R_{11'}$ are independently H, a halogen, hydroxy, amino, $C_1$-$C_5$ alkoxy, benzoyloxy, $R_{14}$C(O)O, wherein $R_{14}$ is H or $C_1$-$C_5$ alkyl; COOH or a salt thereof, SO$_3$H or a salt thereof, PO$_3$H$_2$ or a salt thereof, $C_1$-$C_{24}$ alkyl, COOR$_{15}$ wherein $R_{15}$ is aryl or $C_1$-$C_5$ alkyl; SO$_3$R$_{16}$, wherein $R_{16}$ is aryl or $C_1$-$C_5$ alkyl; C(O)NR$_{17}$R$_{18}$ wherein $R_{17}$ and $R_{18}$ are each independently H, $C_1$-$C_5$ alkyl, aryl or hydroxy; SO$_2$NR$_{19}$R$_{20}$ wherein $R_{19}$ and $R_{20}$ are each independently H, $C_1$-$C_5$ alkyl or aryl; SR$_{21}$ wherein $R_{21}$ is $C_1$-$C_5$ alkyl or aryl; SCH$_2$R$_{25}$, wherein $R_{25}$ is aryl; SC(O)R$_{21}$ wherein $R_{21}$ is as defined above; NR$_{22}$R$_{23}$ wherein $R_{22}$ and $R_{23}$ are each independently H, $C_1$-$C_5$ alkyl or aryl; NHC(O)—$R_{24}$, wherein $R_{24}$ is aryl optionally substituted with COOH or a salt thereof, or $C_1$-$C_7$ alkoxy; O(CH$_2$)$_n$—$R_{26}$—$R_{27}$, wherein n is 1 to 7, $R_{26}$ is aryl, $R_{27}$ is COOH or a salt thereof, B(OH)$_2$ or a salt thereof, nitro, $C_1$-$C_7$ alkoxy or aryl, wherein the aryl of $R_{27}$ is substituted with COOH or a salt thereof, B(OH)$_2$ or a salt thereof, nitro or $C_1$-$C_7$ alkoxy; OC(O)N(H)C(H)($R_{28}$)COOR$_{29}$, wherein $R_{28}$ is an amino acid side chain and $R_{29}$ is H or a $C_1$-$C_4$ alkyl;

wherein at least one of $R_4$ and $R_9$ is OC(O)N(H)C(H)($R_{28}$)COOR$_{29}$, wherein $R_{28}$ is an amino acid side chain and $R_{29}$ is H or a $C_1$-$C_4$ alkyl radical;

$R_{12}$ and $R_{13}$ are $C_1$-$C_7$ alkyl; and

X is a ($C_1$-$C_7$ alkylene) or ($C_1$-$C_7$ alkylene)C(O)NH;

or a pharmaceutically acceptable salt thereof.

Other compounds include, for example, those represented by formulas IV to X in U.S. Pat. No. 5,439,899.

The compounds of the present invention may be synthesized by the skilled artisan as known in the art. Synthesis of carboxybenzyl derivatives may be accomplished, for example, as described in Paul, G. C. (2000) Biorg. Med. Chem. Lett. 10:2149-2152 and Cushman, M. (1998) Biorg. Med. Chem. Lett. 8:833-836. Other synthetic routes for the compounds described herein include those found in Cushman et al. (1999) J. Med. Chem. 42(10):1767-1777; Ruell, J. A. et al. (1999) 64:5858-5866; and U.S. Pat. No. 5,439,899 to Cushman et al. Amino acid derivatives of cosalane may be synthesized utilizing peptide chemistry known in the art, and as described, for example, in Santhosh, K. C. et al. (2000) Bioorg. Med. Chem. Lett. 10:2505-2508.

Suitable salts of the compounds used in the present methods include, without limitation, acetate, adipate, alginate, aspartate, benzoate, butyrate, citrate, fumarate, glycolate, hemisulfate, heptanoate, hexanoate, hydrochloride, hydrobromide, hydroiodide, 2-hydroxyethanesulfonate, lactate, maleate, malonate, methanesulfonate, nicotinate, nitrate, oxalate, palmoate, pectinate, persulfate, hydroxynaphthoate, pivalate, propionate, salicylate, succinate, sulfate, tartrate, thiocyanate, tosylate and undecanoate. Other acids, such as oxalic, while not in themselves pharmaceutically acceptable, can be employed in the preparation of salts useful as intermediates in obtaining the compounds of the invention and their pharmaceutically acceptable acid addition salts. In certain embodiments, the salt is the hydrochloride salt.

Compounds used in the present methods include those having quaternization of any basic nitrogen-containing group therein.

The discussion herein is, for simplicity, provided without reference to stereoisomerism. Those skilled in the art will appreciate that the compounds used in the present methods can contain one or more asymmetric centers and thus occur as racemates and racemic mixtures and single optical isomers. All such isomeric forms of these compounds are expressly included in the present invention.

Unless otherwise stated, structures depicted herein are also meant to include compounds that differ only in the presence of one or more isotopically enriched atoms. For example, compounds having the present structures except for the replacement of hydrogen by deuterium or tritium, or the replacement of a carbon by a $^{13}$C- or $^{14}$C-enriched carbon are within the scope of this invention. Such compounds are useful, for example, as analytical tools or probes in biological assays.

The discussion herein is also provided without reference to polymorphs, hydrates, clathrates, solvates, inclusion compounds, isomers, or other forms of the compound. All such forms of these compounds are expressly included in the present invention.

Further, the compounds used in the present methods include prodrugs of the compounds that are converted to the active compound in vivo. For example, the compound can be modified to enhance cellular permeability (e.g., by esterification of polar groups) and then converted by cellular enzymes to produce the active agent. Methods of masking charged or reactive moieties as a pro-drug are known by those skilled in the art (see, e.g., P. Korgsgaard-Larsen and H. Bundgaard, A Textbook of Drug Design and Development, Reading U.K., Harwood Academic Publishers, 1991).

The term "prodrug" refers to compounds that are rapidly transformed in vivo to yield the parent compound of the above formula, for example, by hydrolysis in blood, see, e.g., T. Higuchi and V. Stella, Prodrugs as Novel delivery Systems, Vol. 14 of the A.C.S. Symposium Series and in Edward B. Roche, ed., Bioreversible Carriers in Drug Design, American Pharmaceutical Association and Pergamon Press, 1987, both of which are incorporated by reference herein. See also U.S. Pat. No. 6,680,299. Exemplary prodrugs include a prodrug that is metabolized in vivo by a subject to an active drug having an activity of the compounds as described herein, wherein the prodrug is an ester of an alcohol or carboxylic acid group, if such a group is present in the compound; an amide of an amine group or carboxylic acid group, if such groups are present in the compound; a urethane of an amine group, if such a group is present in the compound; an acetal or ketal of an alcohol group, if such a group is present in the compound; a N-Mannich base or an imine of an amine group, if such a group is present in the compound; or a Schiff base, oxime, acetal, enol ester, oxazolidine, or thiazolidine of a carbonyl group, if such a group is present in the compound, such as described, for example, in U.S. Pat. Nos. 6,680,324 and 6,680,322.

The term "pharmaceutically acceptable prodrug" (and like terms) as used herein refers to those prodrugs of the compounds of the present invention which are, within the scope of sound medical judgment, suitable for use in contact with the tissues of humans and/or other animals without undue toxicity, irritation, allergic response and the like, commensurate with a reasonable risk/benefit ratio, and effective for their intended use, as well as the zwitterionic forms, where possible, of the compounds of the invention.

In certain embodiments, the compounds used in the methods of the present invention are administered directly to a subject. In some embodiments, the compounds will be suspended in a pharmaceutically-acceptable carrier (e.g., physiological saline) and administered orally or by intravenous infusion, or administered subcutaneously, intramuscularly, intrathecally, intraperitoneally, intrarectally, intravaginally, intranasally, intragastrically, intratracheally, or intrapulmonarily. In another embodiment, the intratracheal or intrapulmonary delivery can be accomplished using a standard nebulizer, jet nebulizer, wire mesh nebulizer, dry powder inhaler, or metered dose inhaler. The agents can be delivered directly to the site of the disease or disorder, such as lungs, kidney, or intestines. The dosage required depends on the choice of the route of administration; the nature of the formulation; the nature of the patient's illness; the subject's size, weight, surface area, age, and sex; other drugs being administered; and the judgment of the attending physician. Suitable dosages for each agent are in the range of 0.01-100 µg/kg. Wide variations in the needed dosage are to be expected in view of the variety of compounds available and the differing efficiencies of various routes of administration. For example, oral administration would be expected to require higher dosages than administration by i.v. injection. Variations in these dosage levels can be adjusted using standard empirical routines for optimization as is well understood in the art. Administrations can be single or multiple (e.g., 2-, 3-, 4-, 6-, 8-, 10-; 20-, 50-, 100-, 150-, or more fold). Encapsulation of the compound in a suitable delivery vehicle (e.g., polymeric microparticles or nanoparticles or implantable devices) may increase the efficiency of delivery, particularly for oral delivery.

As a further aspect, the invention provides pharmaceutical formulations and methods of administering the same to achieve any of the therapeutic effects (e.g., attenuation of GVHD) discussed above. The pharmaceutical formulation may comprise any of the reagents discussed above in a pharmaceutically acceptable carrier.

By "pharmaceutically acceptable" it is meant a material that is not biologically or otherwise undesirable, i.e., the material can be administered to a subject without causing any undesirable biological effects such as toxicity.

The formulations of the invention can optionally comprise medicinal agents, pharmaceutical agents, carriers, adjuvants, dispersing agents, diluents, and the like.

The compounds of the invention can be formulated for administration in a pharmaceutical carrier in accordance with known techniques. See, e.g., Remington, *The Science And Practice of Pharmacy* ($21^{st}$ Ed. 2006). In the manufacture of a pharmaceutical formulation according to the invention, the compound (including the physiologically acceptable salts thereof) is typically admixed with, inter alia, an acceptable carrier. The carrier can be a solid or a liquid, or both, and is preferably formulated with the compound as a unit-dose formulation, for example, a tablet, which can contain from 0.01 or 0.5% to 95% or 99% by weight of the compound. One or more compounds can be incorporated in the formulations of the invention, which can be prepared by any of the well-known techniques of pharmacy.

The formulations of the invention include those suitable for oral, rectal, topical, buccal (e.g., sub-lingual), vaginal, parenteral (e.g., subcutaneous, intramuscular including skeletal muscle, cardiac muscle, diaphragm muscle and smooth muscle, intradermal, intravenous, intraperitoneal), topical (i.e., both skin and mucosal surfaces, including airway surfaces), intranasal, transdermal, intraarticular, intrathecal, and inhalation administration, administration to the liver by intraportal delivery, as well as direct organ injection (e.g., into the liver, into the brain for delivery to the central nervous system, or into the pancreas) or injection into a body cavity. The most suitable route in any given case will depend on the nature and severity of the condition being treated and on the nature of the particular compound which is being used.

For injection, the carrier will typically be a liquid, such as sterile pyrogen-free water, pyrogen-free phosphate-buffered saline solution, bacteriostatic water, or Cremophor EL[R] (BASF, Parsippany, N.J.). For other methods of administration, the carrier can be either solid or liquid.

For oral administration, the compound can be administered in solid dosage forms, such as capsules, tablets, and powders, or in liquid dosage forms, such as elixirs, syrups, and suspensions. Compounds can be encapsulated in gelatin capsules together with inactive ingredients and powdered carriers, such as glucose, lactose, sucrose, mannitol, starch, cellulose or cellulose derivatives, magnesium stearate, stearic acid, sodium saccharin, talcum, magnesium carbonate and the like. Examples of additional inactive ingredients that can be added to provide desirable color, taste, stability, buffering capacity, dispersion or other known desirable features are red iron oxide, silica gel, sodium lauryl sulfate, titanium dioxide, edible white ink and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric-coated for selective disintegration in the gastrointestinal tract. Liquid dosage forms for oral administration can contain coloring and flavoring to increase patient acceptance.

Formulations suitable for buccal (sub-lingual) administration include lozenges comprising the compound in a flavored base, usually sucrose and acacia or tragacanth; and pastilles comprising the compound in an inert base such as gelatin and glycerin or sucrose and acacia.

Formulations of the present invention suitable for parenteral administration comprise sterile aqueous and non-aqueous injection solutions of the compound, which preparations are preferably isotonic with the blood of the intended recipient. These preparations can contain anti-oxidants, buffers, bacteriostats and solutes which render the formulation isotonic with the blood of the intended recipient. Aqueous and non-aqueous sterile suspensions can include suspending agents and thickening agents. The formulations can be presented in unit/dose or multi-dose containers, for example sealed ampoules and vials, and can be stored in a freeze-dried (lyophilized) condition requiring only the addition of the sterile liquid carrier, for example, saline or water-for-injection immediately prior to use.

Extemporaneous injection solutions and suspensions can be prepared from sterile powders, granules and tablets of the kind previously described. For example, in one aspect of the present invention, there is provided an injectable, stable, sterile composition comprising a compound of the invention, in a unit dosage form in a sealed container. The compound or salt thereof is provided in the form of a lyophilizate which is capable of being reconstituted with a suitable pharmaceutically acceptable carrier to form a liquid composition suitable for injection thereof into a subject. The unit dosage form typically comprises from about 1 mg to about 10 grams of the compound or salt. When the compound or salt is substantially water-insoluble, a sufficient amount of emulsifying agent which is pharmaceutically acceptable can be employed in sufficient quantity to emulsify the compound or salt in an aqueous carrier. One such useful emulsifying agent is phosphatidyl choline.

Formulations suitable for rectal administration are preferably presented as unit dose suppositories. These can be prepared by admixing the compound with one or more conventional solid carriers, for example, cocoa butter, and then shaping the resulting mixture.

Formulations suitable for topical application to the skin preferably take the form of an ointment, cream, lotion, paste, gel, spray, aerosol, or oil. Carriers which can be used include petroleum jelly, lanoline, polyethylene glycols, alcohols, transdermal enhancers, and combinations of two or more thereof.

Formulations suitable for transdermal administration can be presented as discrete patches adapted to remain in intimate contact with the epidermis of the recipient for a prolonged period of time. Formulations suitable for transdermal administration can also be delivered by iontophoresis (see, for example, Tyle, *Pharm. Res.* 3:318 (1986)) and typically take the form of an optionally buffered aqueous solution of the compounds. Suitable formulations comprise citrate or bis/tris buffer (pH 6) or ethanol/water and contain from 0.1 to 0.2M of the compound.

The compound can alternatively be formulated for nasal administration or otherwise administered to the lungs of a subject by any suitable means, e.g., administered by an aerosol suspension of respirable particles comprising the compound, which the subject inhales. The respirable particles can be liquid or solid. The term "aerosol" includes any gas-borne suspended phase, which is capable of being inhaled into the bronchioles or nasal passages. Specifically, aerosol includes a gas-borne suspension of droplets, as can be produced in a metered dose inhaler or nebulizer, or in a mist sprayer. Aerosol also includes a dry powder composition suspended in air or other carrier gas, which can be delivered by insufflation from an inhaler device, for example. See Ganderton & Jones, *Drug Delivery to the Respiratory Tract*, Ellis Horwood (1987); Gonda (1990) *Critical Reviews in Therapeutic Drug Carrier Systems* 6:273-313; and Raeburn et al., *J. Pharmacol. Toxicol. Meth.* 27:143 (1992). Aerosols of liquid particles comprising the compound can be produced by any suitable means, such as with a pressure-driven aerosol nebulizer or an ultrasonic nebulizer, as is known to those of skill in the art. See, e.g., U.S. Pat. No. 4,501,729. Aerosols of solid particles comprising the compound can likewise be produced with any solid particulate medicament aerosol generator, by techniques known in the pharmaceutical art.

Alternatively, one can administer the compound in a local rather than systemic manner, for example, in a depot or sustained-release formulation.

Further, the present invention provides liposomal formulations of the compounds disclosed herein and salts thereof. The technology for forming liposomal suspensions is well known in the art. When the compound or salt thereof is an aqueous-soluble salt, using conventional liposome technology, the same can be incorporated into lipid vesicles. In such an instance, due to the water solubility of the compound or salt, the compound or salt will be substantially entrained within the hydrophilic center or core of the liposomes. The lipid layer employed can be of any conventional composition and can either contain cholesterol or can be cholesterol-free. When the compound or salt of interest is water-insoluble, again employing conventional liposome formation technology, the salt can be substantially entrained within the hydrophobic lipid bilayer which forms the structure of the liposome. In either instance, the liposomes which are produced can be reduced in size, as through the use of standard sonication and homogenization techniques.

The liposomal formulations containing the compounds disclosed herein or salts thereof, can be lyophilized to produce a lyophilizate which can be reconstituted with a pharmaceutically acceptable carrier, such as water, to regenerate a liposomal suspension.

In the case of water-insoluble compounds, a pharmaceutical composition can be prepared containing the water-insoluble compound, such as for example, in an aqueous base emulsion. In such an instance, the composition will contain a sufficient amount of pharmaceutically acceptable emulsifying agent to emulsify the desired amount of the compound. Particularly useful emulsifying agents include phosphatidyl cholines and lecithin.

In particular embodiments, the compound is administered to the subject in a therapeutically effective amount, as that term is defined above. Dosages of pharmaceutically active compounds can be determined by methods known in the art, see, e.g., *Remington's Pharmaceutical Sciences* (Maack Publishing Co., Easton, Pa). The therapeutically effective dosage of any specific compound will vary somewhat from compound to compound, and patient to patient, and will depend upon the condition of the patient and the route of delivery. As a general proposition, a dosage from about 0.1 to about 50 mg/kg will have therapeutic efficacy, with all weights being calculated based upon the weight of the compound, including the cases where a salt is employed. Toxicity concerns at the higher level can restrict intravenous dosages to a lower level such as up to about 10 mg/kg, with all weights being calculated based upon the weight of the compound, including the cases where a salt is employed. A dosage from about 10 mg/kg to about 50 mg/kg can be employed for oral administration. Typically, a dosage from about 0.5 mg/kg to 5 mg/kg can be employed for intramuscular injection. Particular dosages are about 1 μmol/kg to 50 μmol/kg, and more particularly to about 22 μmol/kg and to 33 μmol/kg of the compound for intravenous or oral administration, respectively.

In particular embodiments of the invention, more than one administration (e.g., two, three, four, or more administrations) can be employed over a variety of time intervals (e.g., hourly, daily, weekly, monthly, etc.) to achieve therapeutic effects.

The present invention finds use in veterinary and medical applications. Suitable subjects include both avians and mammals, with mammals being preferred. The term "avian" as used herein includes, but is not limited to, chickens, ducks, geese, quail, turkeys, and pheasants. The term "mammal" as used herein includes, but is not limited to, humans, primates, bovines, ovines, caprines, equines, felines, canines, lagomorphs, etc. Human subjects include neonates, infants, juveniles, and adults.

The present invention is more particularly described in the following examples that are intended as illustrative only since numerous modifications and variations therein will be apparent to those skilled in the art.

Example 1

Effect of Cosalane on CCR7

The early homing of donor T cells into recipient secondary lymphoid tissues (SLT) appears to be absolutely required for aGVHD pathogenesis, as recipient animals lacking all lymphoid tissue fail to develop aGVHD following allogeneic transplantation. In keeping with these findings, our group published data showing that donor T cells lacking the chemokine receptor CC-Chemokine Receptor 7 (CCR7) generate greatly attenuated GVHD responses (Coghill et al., Blood 115(23): 4914 (2010)). CCR7 is a G protein-coupled receptor expressed on naïve T cells, B cells, and activated dendritic cells (DCs), and plays a critical role in their trafficking into SLT. In the case of T cells, CCR7 mediates lymphocyte firm arrest on lymph node (LN) high endothelial venules upon exposure to its ligands, CCL19 and CCL21, by stabilizing interactions between T cell LFA-1 and endothelial ICAM-1. In addition, CCR7 functions to mediate T cell chemotaxis to appropriate T cell-rich zones within the LN paracortex after egress from the circulation, and is important for the movement of T cells to their proper anatomical location within the spleen. In our work, we found that $CCR7^{-/-}$ T cells demonstrated an impaired ability to traffic to recipient LNs and abnormal expansion in the host spleen due to inefficient interactions with resident dendritic cells (DCs). As a result, donor T cell numbers were reduced within all recipient lymphoid sites by transplant day +15. This in turn led to reduced CD8 T cell accumulation within GVHD target organs, and less histological injury. Importantly, however, $CCR7^{-/-}$ T cells retained their anti-tumor potential, suggesting different in vivo requirements for tumor eradication versus GVHD induction. In addition, $CCR7^{-/-}$ regulatory T cells ($T_{regs}$) retained their ability to prevent lethal aGVHD in our study.

Perhaps the most important goal of HSCT research is to separate the beneficial anti-tumor effects mediated by donor T cells from the deleterious GVHD responses that they are also capable of producing. The aforementioned data generated in mice using $CCR7^{-/-}$ T cells indicated that this goal might be accomplished by blocking the function of a single chemokine receptor. Unfortunately, there were no drugs or therapeutic antibodies available for clinical use. As a result, we pursued our high throughput screening (HTS) effort to identify novel small molecule antagonists with anti-CCR7 activity. The initial drug discovery process identified cosalane as a CCR7 antagonist. The inhibitory activity of cosalane on human and mouse CCR7 as well as the lack of cytotoxicity is shown in Table 1. A substantial amount of work has subsequently been done with the compound in an effort to prevent acute graft-versus-host disease in mouse bone marrow transplant models.

TABLE 1

| Compound | Human CCR7 $IC_{50}$ (μM) To CCL19 | Human CCR7 $IC_{50}$ (μM) To CCL21 | Murine CCR7 $IC_{50}$ (μM) To CCL19 | Murine CCR7 $IC_{50}$ (μM) To CCL21 | Cytotoxicity (μM) |
|---|---|---|---|---|---|
| Cosalane | 0.207 | 2.66 | 0.193 | 1.98 | >50 (non-toxic) |

Cosalane Impairs CCR7 Dependent Chemotaxis of Human and Murine T Cells

While useful from a screening perspective, our primary reporter assays for the HTS were not physiologic. As a result, it was important to confirm that hits identified in the HTS were active against native CCR7 and could block an actual function mediated by the receptor. For this, we used a well-described trans-well chemotaxis assay system using human H9 cells, a cutaneous T cell lymphoma line known to express high levels of CCR7 and to migrate in response to its ligands (Ott et al., J. Pharmacol. Toxicol. Meth. 51:105 (2005)). In addition, we utilized primary mouse, naïve ($CD25^{neg}$) T cells obtained from C57BL/6 mice. As depicted in FIG. 1A, human H9 cells placed in the upper chambers of the chemotaxis device readily migrated through the separating membrane when CCL19 was present in the lower chamber. Human H9 cells also migrated in response to CCL21, although this agonist was less potent as was the case in our primary HTS assay (FIG. 1B). When cosalane was added to the upper chambers, cell migration in response to CCL19 was inhibited versus DMSO (FIG. 1A). CCL21 driven chemotaxis was also reduced by cosalane, although this did not achieve statistical significance (FIG. 1B). Similarly, murine T cell chemotaxis was also impaired by cosalane in response to both CCL19 and CCL21 (FIGS. 1C-1D).

Cosalane Impairs CCR7 Dependent Chemotaxis of Human and Murine Cells Even when No Longer Present in Solution Cosalane was designed to imbed in the plasma membrane by way of its hydrophobic cholestanol moiety (Cushman et al., J. Med. Chem. 37:3040 (1994)). Based on these data, we hypothesized that cosalane's actions against CCR7 might prove to be durable, and persist even after free cosalane was removed from the chemotaxis media. To evaluate this possibility, human H9 cells were incubated with 10 mcg/ml (13 μM) of cosalane versus DMSO vehicle for one hour and then washed free of the compound. The cells were then placed into the chemotaxis chamber as was done in FIGS. 1A-1D.

As shown in FIGS. 2A-2B, chemotaxis in response to both CCL19 and CCL21 was significantly reduced by cosalane pretreatment alone. Similar experiments were performed with naïve primary mouse T cells. As was the case with the human H9 cells, the chemotaxis of primary murine T cells in response to both CCL19 and CCL21 was significantly reduced by cosalane pretreatment versus DMSO vehicle (FIGS. 2C-2D).

Example 2

Effect of Cosalane on aGVHD

Methods

Mice: C57BL/6 ("B6", $H-2^b$), B6xDBA/2 F1 ("B6D2", $H-2^{bxd}$), BALB/c ($H-2^d$), and NSG mice were purchased from The Jackson Laboratory. Enhanced green fluorescent protein (eGFP) expressing B6 mice were generated as previously prescribed (Panoskaltsis-Mortari et al., *Blood* 103(9):3590 (2004)). $CCR7^{-/-}$ mice were obtained from The Jackson Laboratory that had been backcrossed 4 times onto a C57BL/6 background (B6.129P2-($CCR7^{tm1Dgen}$). These were further backcrossed in our laboratory to eight generations. All animal experiments were performed in accordance with protocols approved by The University of North Carolina Institutional Animal Care and Use Committee.

Transplantation Procedures: Recipient mice were irradiated on transplant day −1. Recipients were then administered T cell depleted (TCD) bone marrow cells +/−$CD25^-$ column-purified conventional T cells ($T_{cons}$) to induce aGVHD as previously described (Wysocki et al., *J. Immunol.* 173: 845 (2004); Carlson et al., *Blood* 113:1365 (2009)). $T_{cons}$ consisted of $CD4^+$ and $CD8^+$ T cells in a 1:1 ratio. For ex-vivo cosalane incubations, cell populations were suspended in serum/protein free injectable saline unless otherwise indicated. They were then incubated with cosalane at varying concentrations or an equal volume of DMSO vehicle for one hour at 37° C. prior to transplant. The cells were then administered immediately to recipients by tail vein injection. For xenograft experiments, human peripheral blood mononuclear cells (PMBCs) were obtained from leukocytes obtained from The Gulf Coast Regional Blood Center using a Ficoll gradient.

Cosalane: Cosalane was obtained from The Southern Research Institute or prepared in house according to published protocols (Cushman et al., *J. Med. Chem.* 37:3040 (1994); Golebiewski et al., Bioorg. Med. Chem. Lett. 3:1739 (1993)). The cosalane derivatives phenylalanine cosalane (p-cosalane) and tert-butyl cosalane (tb-cosalane) were kind gifts from the laboratory of Dr. Mark Cushman.

$T_{con}$ proliferation assay: Purified $CD25^-$ B6 $T_{cons}$ were incubated with cosalane at the indicated concentrations or an equal volume of DMSO vehicle for one hour at 37° C. The cells were then washed and cultured on 24-well plates previously incubated overnight with anti-CD3 and anti-CD28 antibody at 10 µg/ml. The cells were cultured for 72 hours in complete media supplemented with murine interleukin-2 at 100 IUs/ml and then counted using a hemacytometer.

Organ eGFP quantification: Recipient organs were homogenized and absolute eGFP levels determined with an enzyme linked immunosorbent assay (ELISA) kit as described previously (Cell Biolabs) (Coghill et al., *Blood* 115(23):4914 (2010)).

P815 graft-versus-leukemia model and in vivo imaging: Luciferase transfected P815 murine mastocytoma cells ($H-2^d$) were a kind gift from the laboratory of Dr. Jonathan Serody. P815 cells were cultured and then mixed with TCD bone marrow cells prior to transplantation. A tumor dose of $2.5 \times 10^4$ P815 cells was used for all experiments. Recipients were then serially imaged using an IVIS Kinetic Optical real-time imaging system to monitor for in vivo tumor growth twice weekly. For imaging, recipients were dosed with 3 mg of D-luciferin (Perkin Elmer) by intraperitoneal injection 10 minutes prior to the procedure. Mice were then anesthetized with isoflurane during image acquisition. Unless otherwise indicated an exposure time of 4 seconds was used for all images.

Murine cytomegalovirus experiments: Murine cytomegalovirus (mCMV), Smith strain (VR-1399), was obtained from The American Type Culture Collection ATCC (Manassas VA) and grown on murine 3T3 fibroblasts. For plaque assays, 3T3 cells were grown to 80% confluence on 6 well plates in DMEM (Gibco) supplemented with 10 percent Fetal Bovine Serum (FBS). The culture media was subsequently aspirated off and the cells were incubated in serum free media containing cosalane, p-cosalane, or tb-cosalane at 15 µg/ml for one hour at 37° C. This media was then aspirated off and the cells were cultured in mCMV infectivity media (DMEM plus 2 percent FBS) containing virus at the indicated multiplicity of infection overnight. Infectivity media also contained cosalane, p-cosalane, or tb-cosalane at 15 µg/ml. The next day the infectivity media was aspirated off and the cells layered with 2 ml/well of viscous medium. The cells were subsequently cultured for 6 days, after which plaques were visualized by microscopy and counted.

Epstein Barr experiments: Infectious EBV (B95.8 strain) was produced by induction of the lytic cycle in 293 $EBV^+$ cells by transfection with the viral transactivator BZLF1 (Delecluse et al., *Proc. Natl. Acad. Sci. USA* 95:8245 (1998)). This cell line contains the EBV genome in an inducible EBV bacmid construct which also encodes for GFP. 72 h after viral reactivation with BZLF1, supernatant fluids were harvested, cleared by centrifugation at 500 g for 5 min, and concentrated by centrifugation using an Amicon Ultra 15 100-kDa-molecular-mass-cutoff filter (Millipore). For viral infectivity titration, Raji cells (ATCC) were cultured in serum free RPMI media containing cosalane, p-cosalane, or tb-cosalane at 20 µg/ml or an equal volume of DMSO vehicle for one hour. The cells were then washed with PBS and seeded in culture plates ($2 \times 10^5$ cells/well) with fresh RPMI containing cosalane, p-cosalane, or tb-cosalane at 20 µg/ml or an equal volume of DMSO vehicle and immediately infected with 100 µl of concentrated supernatant fluids containing the $GFP^+$ EBV. Raji cells were treated with 50 ng/ml phorbol-12-myristate-3-acetate and 3 mM sodium butyrate 24 h after infection. At 48 h post-infection, infectious titers were determined by detection of GFP-encoding EBV genomes by flow cytometry. The percentage of cells infected was determined by GFP positivity (Whitehurst et al., *MBio* 6(5):e01574 (2015)).

Statistical Analysis: Statistical analysis was performed using Graphpad Prism. Survival curves were constructed using the method of Kaplan and Meier and median survival times compared using the log-rank test. Unless otherwise indicated, continuous variables were compared using the non-parametric Mann-Whitney test. P values less than 0.05 were considered significant. Error bars represent SEM.

Results

To study aGVHD in mice, recipient animals are lethally irradiated to simulate the pre-transplant chemotherapy or irradiation that human patients receive to eradicate their hematologic malignancy and to make space for the new, donor bone marrow. In these models, genetically mismatched donor and recipient strains are used. As a result, immune cells from the donor strain can recognize the recipient animals as "foreign" and mount inflammatory responses after transplantation.

In our mouse transplantation experiments, we typically study three separate groups in any given transplant. The first group receives only immature bone marrow cells without T cells, the immune cells that induce aGVHD. As a result, these mice almost universally survive the transplant without evidence of aGVHD, and serve as our negative disease controls.

A second group of mice receives bone marrow cells and a dose of unmanipulated, purified, mature donor T cells. These mice develop aGVHD which is lethal in the majority of cases.

A third group, the experimental group, receives bone marrow cells and mature T cells plus an intervention to hopefully limit disease. In this instance, our intervention is the use of cosalane which is described below.

Figures 3B, 3C:
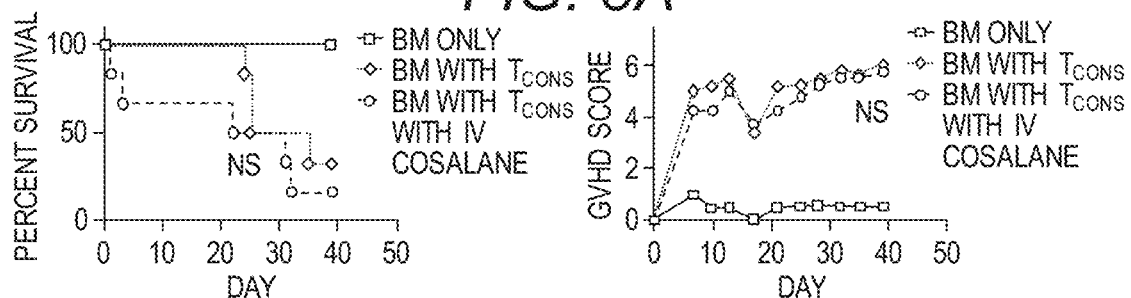
Figures 3D, 3E:
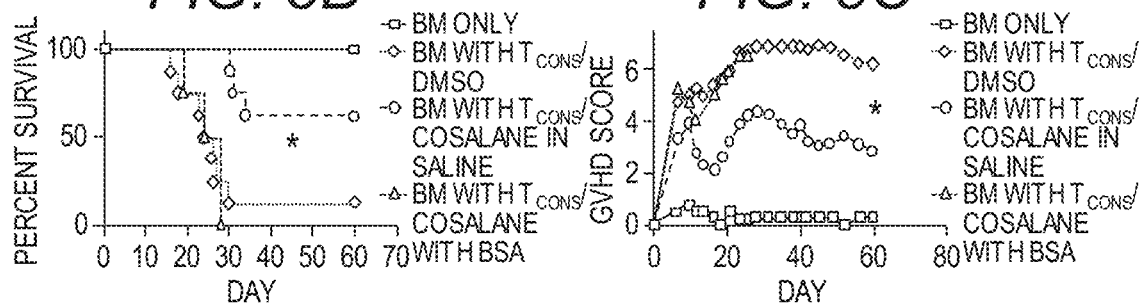

Cosalane does not Prevent aGVHD when Dosed Systemically to Mice after Transplant but is Active Ex Vivo Initial work focused on whether cosalane (structure depicted in FIG. 3A) could limit aGVHD when dosed to murine recipients after HSCT. For these experiments we used a standard C57BL/6 ("B6" $H-2^b$) into C57BL/6×DBA2 F1 ("B6D2" $H-2^{bxd}$) haplotype model system. Based on the limited existing literature describing cosalane administration to rodents (Kuchimanchi et al., Drug Metab. Dispos. 28(4): 403 (2000)), we dosed the compound at 10 mg/kg via intravenous injection on the day of transplant and then again every three days for a total of three doses. Control mice were administered an equivalent volume of dimethyl sulfoxide (DMSO) vehicle. Mice were then followed for overall survival and scored for aGVHD twice weekly using a validated scoring system (van Den Brink et al., J. Immunol. 164:469 (2000)). As depicted in FIGS. 3B and 3C, cosalane did not attenuate aGVHD and may have actually worsened clinical outcomes. Subsequent work has revealed that 10 mg/kg was an excessively high dose to administer to irradiated recipients and that dosages of between 0.5-2 mg/kg are much better tolerated. Nevertheless, given the technical challenges of repeated intravenous drug administration and cosalane supply considerations, we explored the use of an ex vivo dosing strategy as an alternative means to apply the compound. For these experiments, purified $T_{cons}$ were incubated with cosalane at 10 μg/ml (13 μM) or DMSO vehicle diluted in saline at 37° C. for one hour immediately prior to transplant. They were then mixed with untreated T cell depleted (TCD) BM cells and administered to recipients by tail vein injection. Given cosalane's known propensity to bind to serum albumin (Kuchimanchi et al., J. Pharm. Sci. 90(5):659 (2001)), we also evaluated the effects of solubilized protein on compound efficacy by including two separate cosalane treatment groups: one with compound diluted in saline alone and one in saline supplemented with 1% albumin. Recipients received no additional cosalane after transplant. As depicted in FIGS. 3D and 3E, control mice given $T_{cons}$ incubated with DMSO in saline developed aggressive aGVHD and demonstrated poor survival. In contrast, those receiving $T_{cons}$ incubated with cosalane in saline alone demonstrated reduced aGVHD scores and improved median survival times. Notably, mice given $T_{cons}$ incubated with cosalane diluted in saline plus albumin developed severe aGVHD similar to DMSO controls and confirmed that cosalane's high protein avidity could indeed limit its efficacy. As a result, all future cosalane ex vivo incubations were performed in normal saline alone without albumin or serum.

Figures 3F, 3G:
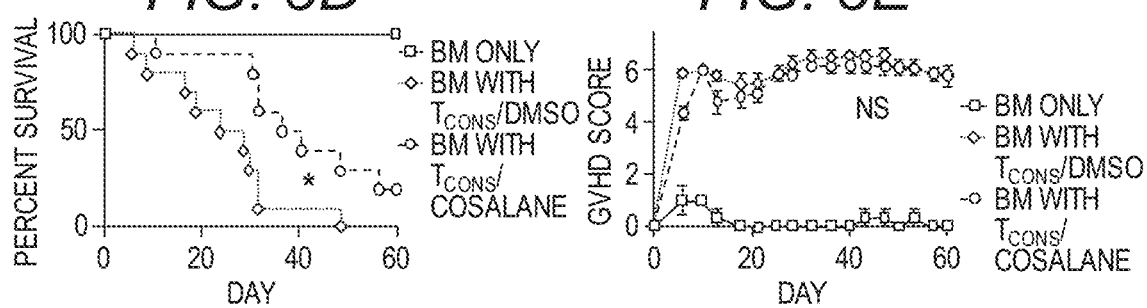
Figures 3H, 3I:
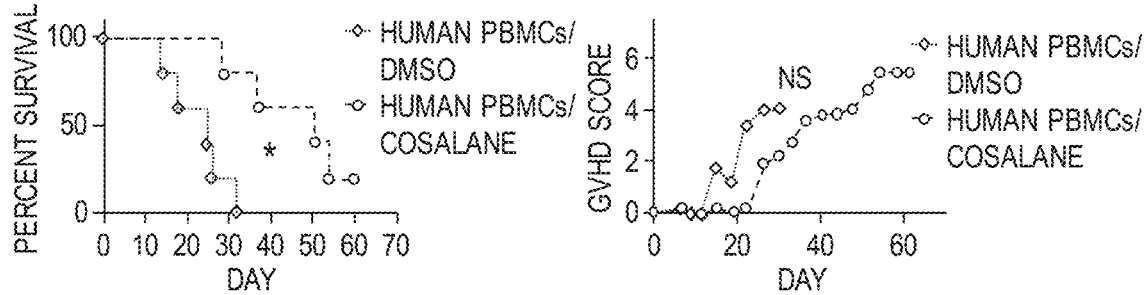

Next, we wished to ensure that cosalane's ability to attenuate aGVHD was not strain dependent. For this work, we used a completely MHC mismatched B6 into BALB/c ($H-2^d$) allograft model (FIGS. 3F and 3G) and a human xenogeneic aGVHD system (FIGS. 3H and 3I). While cosalane's effects were not as complete in these highly aggressive models, in both instances mice receiving cosalane treated cells demonstrated prolonged survival times. Collectively these data indicated that a brief incubation of donor immune cells with cosalane in a protein-free vehicle could reduce aGVHD and that this effect did not appear to be strain or species specific.

Cosalane Exposure does not Result in Cytotoxicity or Impair Bone Marrow Engraftment Previous reports have indicated that cosalane is non-toxic to cells in vitro with a therapeutic index >100 (Cushman et al., J. Med. Chem. 37:3040 (1994)). Nevertheless, we set out to ensure that cosalane's ability to prevent aGVHD was not the result of the drug killing the donor $T_{con}$ inoculum or limiting their intrinsic ability to undergo activation and expansion. Purified B6 $T_{cons}$ were isolated as before and incubated with cosalane at increasing concentrations ranging from 10 μg/ml (13 μM—the concentration used for the B6 into B6D2 survival experiment described in FIGS. 3D and 3E) to 30 μg/ml (39 μM) or an equal volume of DMSO diluted in normal saline. The cells were then washed, placed on 24 well plates pre-coated with anti-CD3 and anti-CD28 immunoglobulin, and cultured for 72 hours in media containing supplemental IL-2. Following the incubation all of the $T_{con}$ groups exhibited robust growth in vitro and no differences in cell numbers were noted after the culture period (FIG. 4A).

Following up on these data, we determined whether cosalane exposure would potentially cause injury to hematopoietic stem cells if bone marrow were also exposed to cosalane ex vivo. Notably, this situation would be potentially relevant to human transplantation where the donor stem cell product is typically not separated into separate cellular components prior to administration. Purified $T_{cons}$ and TCD BM cells were obtained from B6 donors transgenic for enhanced green fluorescent protein (eGFP+) and were mixed together prior to being incubated with cosalane or DMSO. The cells were subsequently administered to irradiated B6D2 recipients and both bone marrow and $T_{con}$ engraftment then determined by flow cytometry within the host spleen on transplant day +10. Donor derived cells were distinguished from residual host cells by virtue of their eGFP positivity. As depicted in FIG. 4B, cosalane exposure did not produce any differences in donor monocyte, neutrophil, T cell, or B cell numbers in the spleen at this time point.

Next, we determined if cosalane treatment of the entire stem cell product (BM plus $T_{cons}$) would limit the compound's ability to reduce aGVHD or potentially result in late mortality due to bone marrow failure. As depicted in FIGS. 4C and 4D, cosalane treatment of the whole stem product appeared to attenuate aGVHD at least as well as what was observed previously with the isolated treatment of $T_{cons}$ alone. Furthermore, no clinical signs of delayed bone marrow failure were observed with 90% of the cosalane group surviving to the end of the study observation period. Collectively, these data indicated that cosalane did not induce any apparent cytotoxicity in vitro at doses up to 39 μM and that a whole marrow product could be safely exposed to compound without any loss of compound efficacy or an impairment in myeloid or lymphoid engraftment.

Figure 5A:
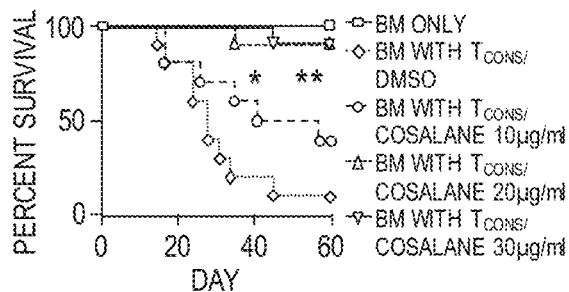
FIGS. 5A-5J show cosalane attenuates aGVHD in a dose dependent fashion and is more potent than two structurally similar derivatives. (A, B) B6D2 mice were lethally irradiated on transplant day −1. On day 0 recipients were administered $3\times10^6$ TCD B6 BM cells +/−$4\times10^6$ B6 $T_{cons}$. Donor $T_{cons}$ were incubated ex vivo with DMSO vehicle or cosalane diluted in normal saline at increasing concentrations ranging from 10 µg/ml to 30 µg/ml. The cells were then mixed with untreated TCD B6 BM cells and administered immediately to recipient mice by tail vein injection. Mice were then followed for survival and scored for aGVHD. N=4 BM only. N=10 for all other treatment groups. (A) *P=020 for survival curve comparison between BM with $T_{cons}$/cosalane 10 µg/ml and BM with $T_{cons}$/cosalane 20 µg/ml. **P=0.0165 for survival curve comparison between BM with $T_{cons}$/cosalane 10 µg/ml and BM with $T_{cons}$/cosalane 30 µg/ml. (B) P>0.05 for aGVHD score comparison between BM with $T_{cons}$/cosalane 10 µg/ml and BM with $T_{cons}$/cosalane 20 µg/ml or BM with $T_{cons}$/cosalane 30 µg/ml on transplant day +60. (C, D) BALB/c mice were irradiated to 800 rads on transplant day −1. On day 0 recipients were administered $5\times10^6$ TCD B6 BM cells +/−$5\times10^5$ whole B6 $T_{cons}$. Donor $T_{cons}$ were incubated ex vivo with DMSO vehicle or cosalane diluted in normal saline at 30 µg/ml. The cells were then mixed with untreated TCD B6 BM cells and administered immediately to recipient mice by tail vein injection. Mice were then followed for survival and scored for aGVHD. N=4 BM only. N=9 BM with $T_{cons}$/DMSO. N=10 BM with $T_{cons}$/cosalane. (C) *P<0.0001 for survival curve comparison between BM with $T_{cons}$/DMSO and BM with $T_{cons}$/cosalane groups. (D) *P<0.0001 for aGVHD score comparison between BM with $T_{cons}$/DMSO and BM with $T_{cons}$/cosalane groups on day +35. (E, F) NSG mice were irradiated to 200 rads on transplant day −1. On day 0 recipients were administered $7\times10^6$ human peripheral blood mononuclear cells incubated ex vivo with DMSO or cosalane at 35 µg/ml. Mice were then followed for survival and scored for aGVHD. N=6 mice per treatment group. (E) *P=0.0049 for survival curve comparison. (F) P>0.05 for aGVHD score comparison between Human PBMCs/DMSO group and Human PBMCs/cosalane group on day +45. (G, H) B6D2 mice were lethally irradiated on transplant day −1. On day 0 recipients were administered $3\times10^6$ TCD B6 BM cells +/−$4\times10^6$ B6 $T_{cons}$. Donor $T_{cons}$ were incubated ex vivo with DMSO vehicle or cosalane, p-cosalane, or tb-cosalane diluted in normal saline at 20 µg/ml. The cells were then mixed with untreated TCD B6 BM cells and administered immediately to recipient mice by tail vein injection. Mice were then followed for survival and scored for aGVHD. N=2 BM only. N=4 for all other treatment groups. (G) *P=040 for survival curve comparison between BM with $T_{cons}$/DMSO and BM with $T_{cons}$/cosalane. P>0.05 for survival curve comparison between BM with $T_{cons}$/DMSO and BM with $T_{cons}$/p-cosalane or BM with $T_{cons}$/tb-cosalane. (H) P>0.05 for aGVHD score comparison between BM with $T_{cons}$/DMSO and BM with $T_{cons}$/p-cosalane on day +62 and between BM with $T_{cons}$/DMSO and BM with $T_{cons}$/tb-cosalane on day +38. (I, J) B6D2 mice were lethally irradiated on transplant day −1. On day 0 recipients were administered $3\times10^6$ TCD B6 BM cells +/−$4\times10^6$ B6 $T_{cons}$. Donor $T_{con}$, were incubated ex vivo with DMSO vehicle or p-cosalane or tb-cosalane diluted in normal saline at 30 µg/ml. The cells were then mixed with untreated TCD B6 BM cells and administered immediately to recipient mice by tail vein injection. Mice were then followed for survival and scored for aGVHD. N=2 BM only. N=5 for all other treatment groups. (I) *P=0269 for survival curve comparison between BM with $T_{cons}$/DMSO and BM with $T_{cons}$/p-cosalane. **P=0.0039 for survival curve comparison between BM with $T_{cons}$/DMSO and BM with $T_{cons}$/tb-cosalane. (J) P=0.0079 for aGVHD score comparison between BM with $T_{cons}$/DMSO and BM with $T_{cons}$/p-cosalane on day +41. P=0.0238 for aGVHD score comparison between BM with $T_{cons}$/DMSO and BM with $T_{cons}$/tb-cosalane on day +41.
Figure 5B:
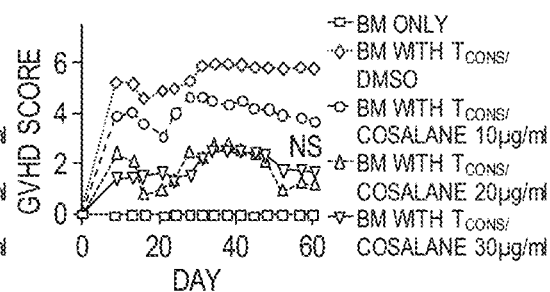

Cosalane Attenuates aGVHD in a Dose Dependent Fashion and is More Potent than Two Similar Structural Derivatives Next, we set out to formally determine if cosalane's ability to attenuate aGVHD was dose dependent. For this work we incubated purified B6 $T_{cons}$ with DMSO or increasing concentrations of cosalane ex-vivo: 10 µg/ml (13 µM), 20 µg/ml (26 µM) or 30 µg/ml (39 µM). The cells were then mixed with untreated TCD B6 BM cells and administered to irradiated B6D2 recipients. Recipient mice were followed for survival and scored for aGVHD twice weekly. As depicted in FIGS. 5A and 5B, we observed improved transplant outcomes with increasing dosages of cosalane during the pre-incubation step. Building on these data, we went on to repeat transplants using a B6 into BALB/c completely MHC mismatched allograft model (FIGS. 5C and 5D) and a human PBMC into NSG xenogeneic system (FIGS. 5E and 5F) with higher compound doses. Compared to the outcomes observed previously in FIGS. 3F-3I, cosalane's effects were more complete and durable with most recipients surviving to the end of the study period. Thus, at higher dosages cosalane allowed for nearly complete aGVHD protection in three separate model systems.

Our laboratory subsequently evaluated the activity of two cosalane derivatives: phenylalanine cosalane (p-cosalane) and tert-butyl cosalane (tb-cosalane) in which the amino acid phenylalanine or a tert-butyl group respectively is conjugated to each of cosalane's two carboxylic acid groups. For this work we used a B6 into B6D2 model system and incubated donor $T_{cons}$ ex vivo with identical doses of either cosalane, p-cosalane, tb-cosalane, or DMSO vehicle prior to transplant. Recipients were then followed for survival and scored for aGVHD. As depicted in FIGS. 5G and 5H, neither derivative appeared to be as active as the parent compound. Given the dose dependent nature of cosalane's aGVHD protective effects, however, we repeated this experiment with higher concentrations of each derivative. As shown in FIGS. 5I and 5J, both structures were able to improve median survival times at higher doses, with recipients of p-cosalane treated $T_{cons}$ showing the lowest aGVHD scores. Collectively, these data indicated a class effect for this family of compounds. Nevertheless, neither of the derivatives were as potent as the parent structure, suggesting that the identity of the compound's hydrophilic head group is particularly relevant to the drug's ability to ameliorate aGVHD after HSCT.

Cosalane Limits aGVHD by Acting on Donor $T_{cons}$ and Blocks their Accumulation within the Colon and Liver Most of our allogeneic transplantation experiments up to this point had involved the treatment of purified donor $T_{cons}$ made up of a mixture of CD25⁻CD4⁺ and CD25⁻CD8⁺ cells (FIGS. 3D-3G, FIGS. 5A-5D). In treating this particular population we were able to consistently reduce aGVHD and improve survival, thereby establishing donor $T_{cons}$ as a critical cosalane drug target. Previous studies, however, have shown that donor bone marrow derived antigen presenting cells and in particular CCR7⁺ dendritic cells play a role in augmenting the aGVHD process (Matte et al., Nat. Med. 10(9):987 (2004); Koyama et al., J. Exp. Med. 212(8): 1303 (2015)). Furthermore, in our own experiments in which donor BM cells and donor $T_{cons}$ were both exposed to cosalane pre-transplant (FIGS. 4C and 4D) we achieved excellent long term aGVHD control. As a result, we questioned whether recipient mice might derive benefit from the isolated treatment of donor BM cells alone or synergistic benefit from the combined treatment of donor $T_{cons}$ and marrow. To formally evaluate this possibility, we performed a B6 into B6D2 haplotype matched transplant in which we pretreated either donor BM cells, donor $T_{cons}$, both populations, or neither with cosalane prior to HSCT. Notably, since we demonstrated cosalane's effects to be dose dependent, each cell population(s) was incubated in an identical concentration of drug. Recipients were then followed for survival and scored for aGVHD twice weekly. As shown in FIGS. 6A and 6B, the isolated treatment of purified donor BM cells alone did not significantly improve outcomes. Conversely, the isolated treatment of donor $T_{cons}$ once again resulted in a substantial attenuation of aGVHD with 100% survival in this instance. Notably, the combined treatment of BM cells and $T_{cons}$ did not appear to further reduce aGVHD scores. Nevertheless, the combination group appeared to do equally well with 100% of recipients surviving to the end of the study period. Collectively, these data confirmed our previous findings that cosalane can be safely administered to a whole donor stem cell product (BM cells plus T cells) but simultaneously indicated that cosalane's protective effects occur primarily via action on mature $T_{cons}$ contained in the graft.

Figure 6A:
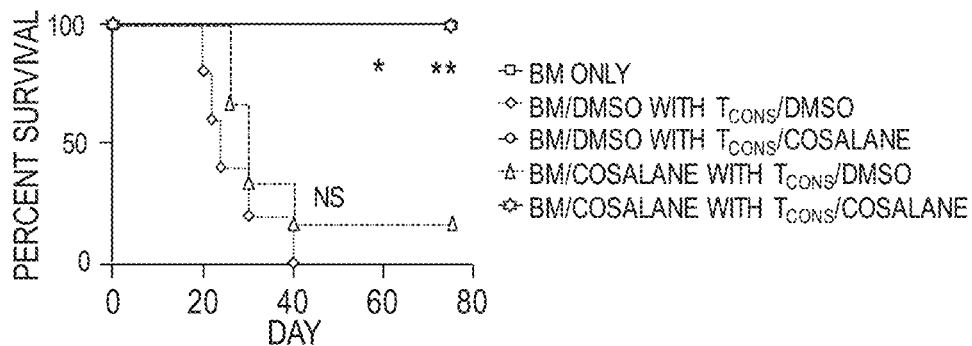
FIGS. 6A-6F show cosalane attenuates aGVHD by limiting donor $T_{con}$ accumulation within the liver and colon. (A, B) B6D2 mice were lethally irradiated on transplant day −1. On day 0 recipients were administered $3\times10^6$ TCD B6 BM cells +/−$4\times10^6$ B6 $T_{cons}$. Donor TCD BM cells, donor $T_{cons}$, both cell populations, or neither were incubated ex vivo with cosalane at 15 µg/ml for one hour prior to transplant. Those cells not treated with cosalane were incubated with an equal volume of DMSO vehicle. Mice were then followed for survival and scored for aGVHD. N=2 BM only. N=5 for all other treatment groups. (A) P>0.05 for survival curve comparison between BM/DMSO with $T_{cons}$/DMSO and BM/cosalane with $T_{cons}$/DMSO groups. *P=0.0018 for survival curve comparison between BM/DMSO with $T_{cons}$/DMSO and BM/DMSO with $T_{cons}$/cosalane groups. **P=0.0018 or survival curve comparison between BM/DMSO with $T_{cons}$/DMSO and BM/cosalane with $T_{cons}$/cosalane groups. (B) P>0.05 for aGVHD score comparison between BM/DMSO with $T_{cons}$/DMSO and BM/cosalane with $T_{cons}$/DMSO groups on transplant day +40. (C, D) B6D2 mice were lethally irradiated on transplant day −1. On day 0 recipients were administered $3\times10^6$ TCD eGFP$^-$ B6 BM cells plus $4\times10^6$ eGFP$^+$ B6 $T_{cons}$. Donor $T_{cons}$ were incubated ex vivo with DMSO vehicle or cosalane diluted in normal saline at 15 µg/ml. The cells were then mixed with untreated TCD B6 BM cells and administered immediately to recipient mice by tail vein injection. Recipient mice were subsequently killed on day +7 (C) or day +14 (D). Lymphoid organs (left panels) and aGVHD target organs (right panels) were subsequently harvested and homogenized. Total eGFP levels were then determined using an anti-eGFP ELISA. N=7 per treatment group. (C) P>0.05 for all pairwise comparisons on day +7. (D) *P=0.0003 for colon comparison between DMSO and cosalane groups by Mann-Whitney test. **P=0.0006 for liver comparison. (E, F) B6D2 mice were transplanted as in (C, D) and their organs removed and homogenized on day +7 (E) or day +14 (F). Total IFN-γ (left panels) and TNF (right panels) was then determined by ELISA. N=7 per treatment group. (E) *P=0.038 for total TNF comparison in the liver on day +7 by Mann-Whitney test. (F) *P=0.0015 for total IFN-γ comparison in the colon on day +14. **P=0.0002 for total TNF comparison in the colon on day +14.
Figure 6B:
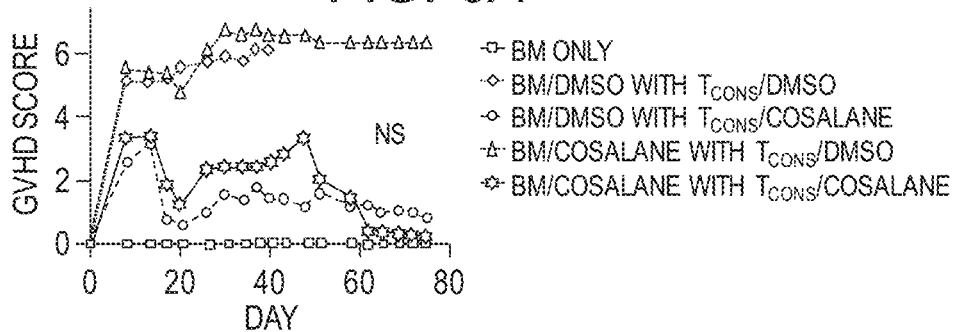
Figure 6C:
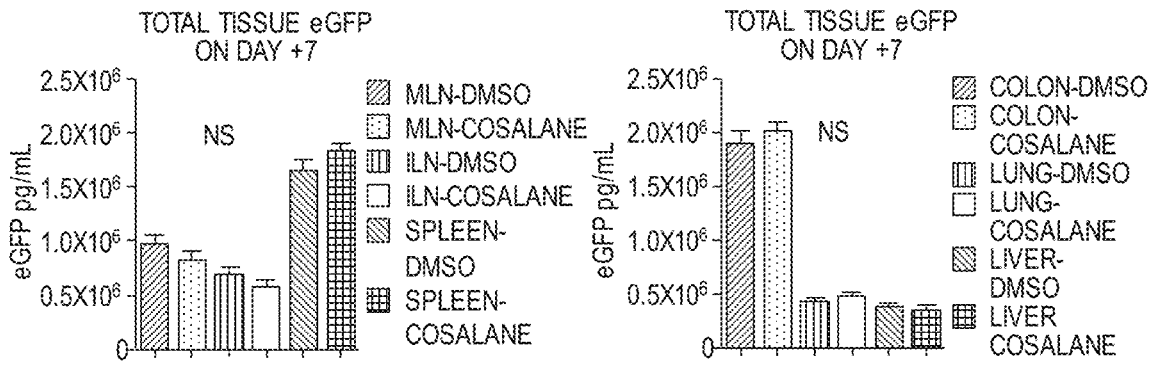

Given that cosalane appeared to act primarily on $T_{cons}$, we elected to focus on this population for the remainder of our studies. Since cosalane was known to block CCR7 in vitro (Hull-Ryde et al., SLAS Discovery 2018. Jun. 1. Epub ahead of print), we hypothesized that the compound would limit donor $T_{con}$ trafficking to host lymph nodes after transplant (Coghill et al., Blood 115(23): 4914 (2010); Forster et al., Cell 99(1):23 (1999)). To evaluate this, eGFP⁺ B6 $T_{cons}$ were incubated with cosalane or DMSO vehicle and then transplanted with untreated eGFP⁻ B6 TCD BM cells into irradiated eGFP⁻ B6D2 recipients. On day +7 recipients were killed and their secondary lymphoid organs removed (mesenteric lymph nodes, inguinal lymph nodes, and spleen) along with three important aGVHD target organs (colon, lung, and liver). These tissues were then homogenized and donor $T_{con}$ accumulation in each site compared between recipients of cosalane versus vehicle treated cells using an anti-eGFP ELISA approach. As depicted in FIG. 6C, no differences in donor $T_{con}$ accumulation were noted in either host secondary lymphoid tissues (left panel) or aGVHD target organs (right panel) at this time point.

Figure 6D:
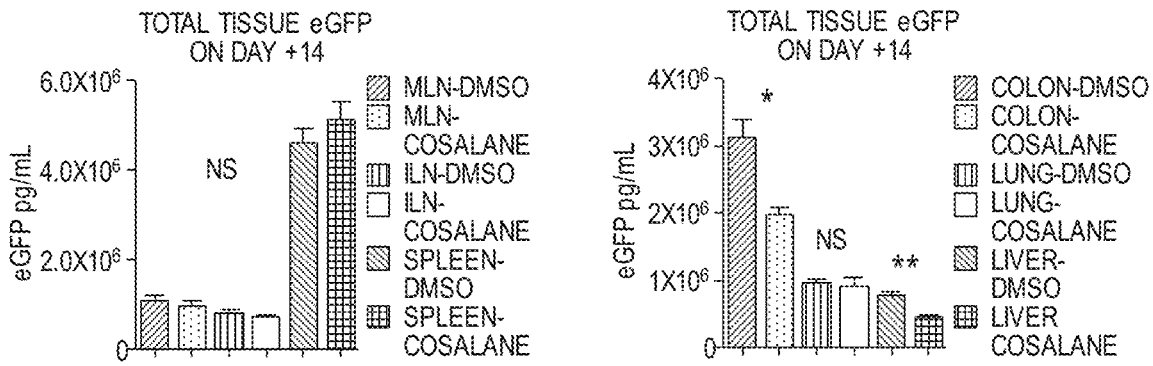

Subsequent to this we performed an identical transplant but harvested recipient organs on day +14, a later time point when clinical differences between the two treatment groups are typically more prominent (FIG. 6D). As before, no differences in donor $T_{con}$ accumulation were noted within host lymphoid sites (left panel). However, by the second transplant week we detected a significant reduction in donor $T_{cons}$ within the colon and liver (right panel). Together these experiments supported two conclusions. First, consistent with our in vitro cell culture data (FIG. 4A) and flow cytometry reconstitution experiments (FIG. 4B), cosalane was not causing any generalized deficit in $T_{con}$ expansion as the eGFP signal was similar within a majority of sites in both treatment groups. Instead, cosalane was specifically limiting donor $T_{con}$ accumulation in two critical aGVHD target organs while having surprisingly little impact on their expansion within SLT.

Figure 6E:
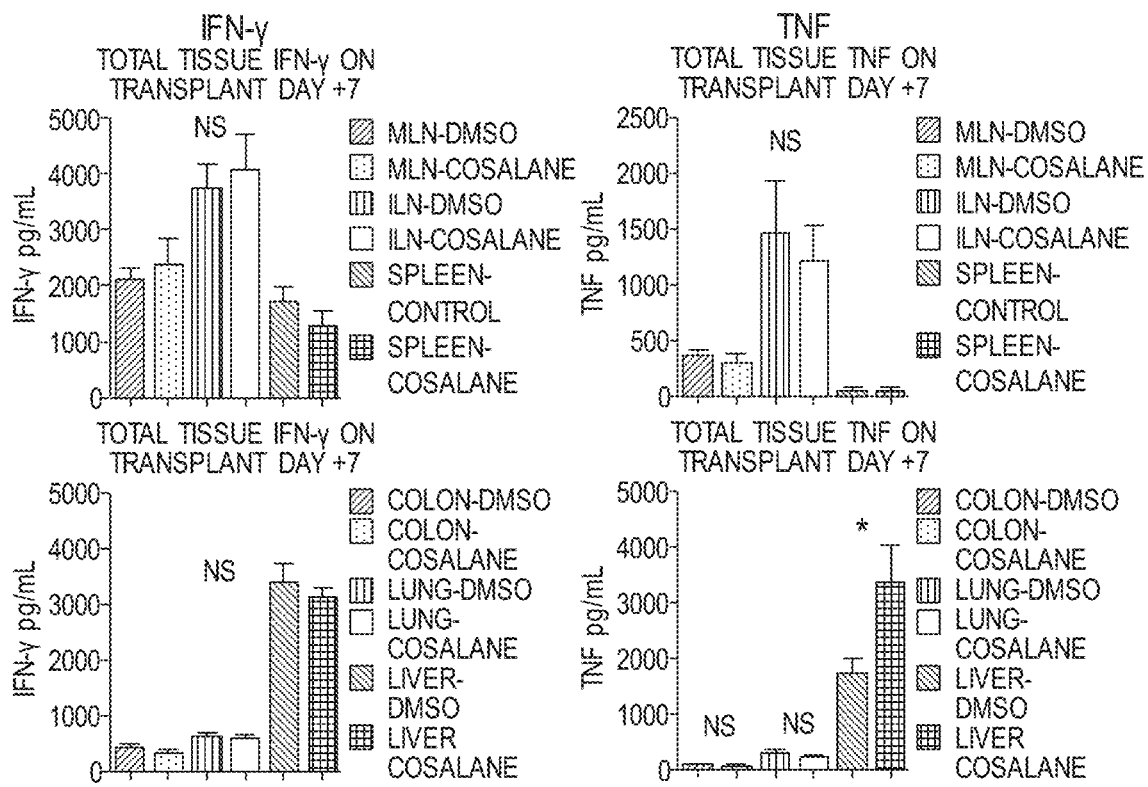
Figure 6F:
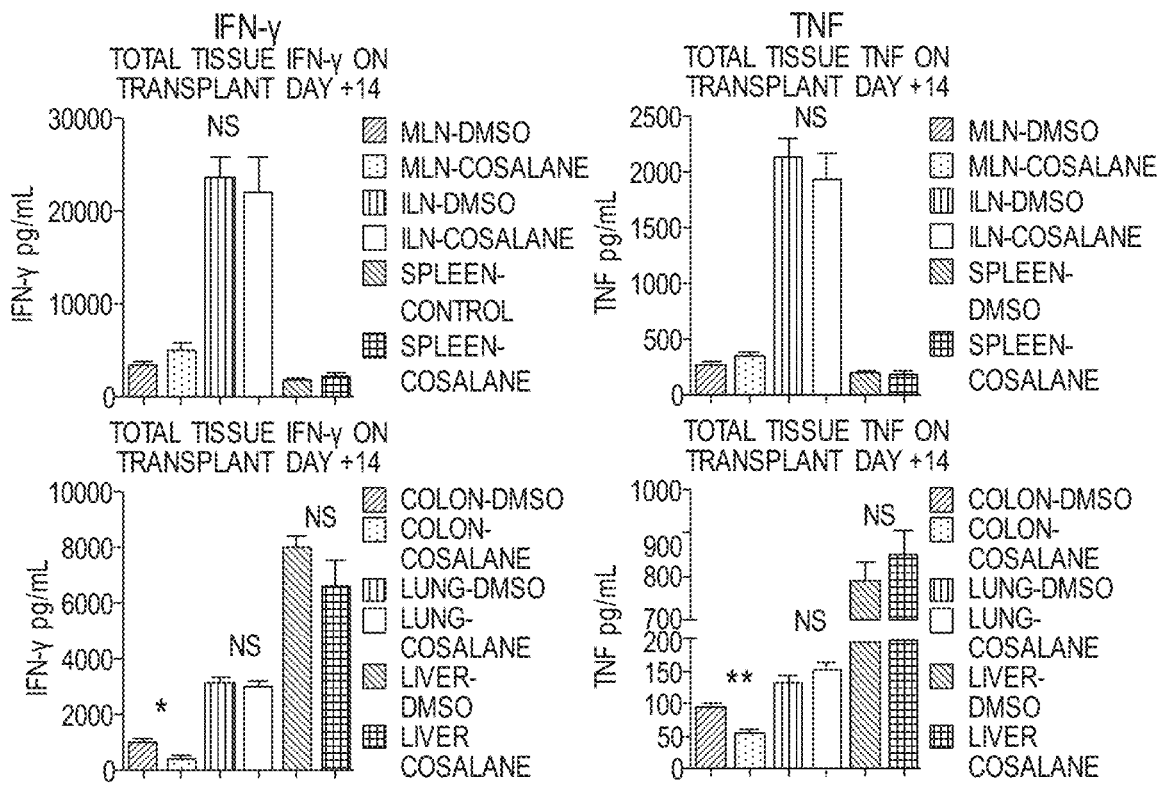

Following up on these data, we evaluated cosalane's effects on inflammatory cytokine production after HSCT. No differences in total TNF or IFN-γ levels were noted in the spleen, MLN, ILNs, or lung on either transplant day +7 (FIG. 6E) or day +14 (FIG. 6F). Conversely, consistent with our $T_{con}$ in vivo trafficking data, both TNF and IFN-γ levels were significantly reduced in the host colon on day +14 in the cosalane treatment group (FIG. 6F, bottom panels). Collectively these data do not support any generalized deficiency in inflammatory cytokine production following cosalane exposure. Rather, with the exception of the liver, they indicated that organ cytokine level differences between the cosalane and control groups generally paralleled differences in the number of infiltrating donor $T_{cons}$.

Cosalane Prevents aGVHD by Blocking CCR7 on Donor $T_{cons}$

As described previously, our initial premise for using cosalane to attenuate aGVHD was based on its demonstrable antagonist effects on CCR7, a chemokine receptor critical for T cell trafficking into secondary lymphoid tissues (Forster et al., *Cell* 99(1):23 (1999)). Nevertheless, our in vivo trafficking data indicated a minimal impact on the ability of donor $T_{cons}$ to accumulate within the host spleen or lymph nodes on transplant days +7 and +14 and suggested that cosalane's anti-aGVHD properties might ironically be CCR7 independent. To more definitively ascertain the extent to which cosalane's protective effects were linked to CCR7 we induced lethal aGVHD with CCR7$^{-/-}$ $T_{cons}$, reasoning that if CCR7 were indeed critical for its action the drug should be less active in this setting. Notably, aGVHD is not entirely prevented by the genetic absence of CCR7 on donor $T_{cons}$. Rather, aGVHD is greatly attenuated compared to that induced by an equivalent dose of wild-type (WT) donor $T_{cons}$. Previously, we found that the degree of aGVHD attenuation that is observed in the absence of CCR7 is somewhat model dependent with outcome differences being less pronounced with higher degrees of MHC mismatch between the donor and recipient strains (Coghill et al., *Blood* 115(23): 4914 (2010)). As a result, for this work we chose an aggressive completely MHC mismatched B6 into BALB/c system, and increased our standard WT donor $T_{con}$ dose from 5×10$^5$ cells per recipient to 3×10$^6$ CCR7$^{-/-}$ B6 $T_{cons}$ per recipient in order to consistently induce lethal aGVHD in control mice. CCR7$^{-/-}$ $T_{cons}$ were pretreated with DMSO or cosalane ex vivo at 15 µg/ml, the same dose that we had used for the survival studies depicted in FIGS. 3F and 3G using an identical B6 into BALB/c strain combination. As depicted in FIGS. 7A and 7B and in contrast to what was observed with WT B6 donor $T_{cons}$, cosalane appeared to be completely inactive at this dose.

Figure 5C:
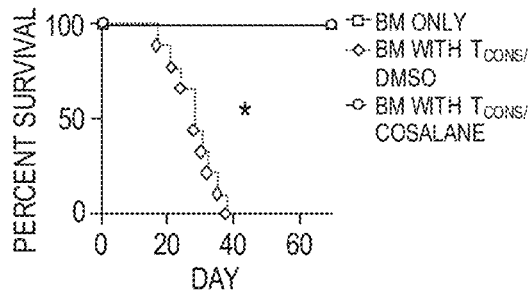
Figure 5D:
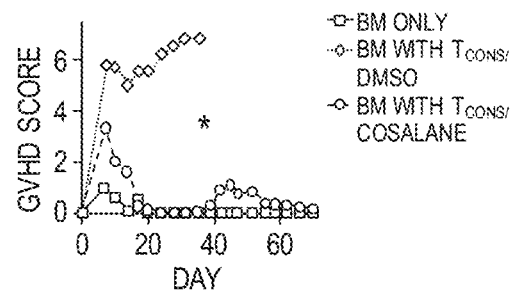
Figure 5E:
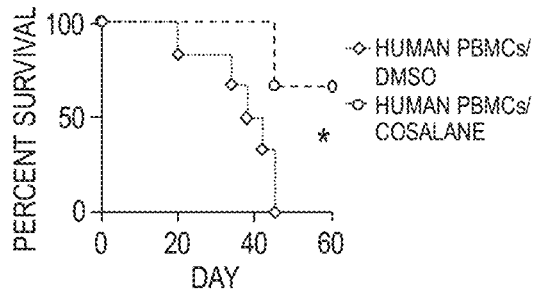
Figure 5F:
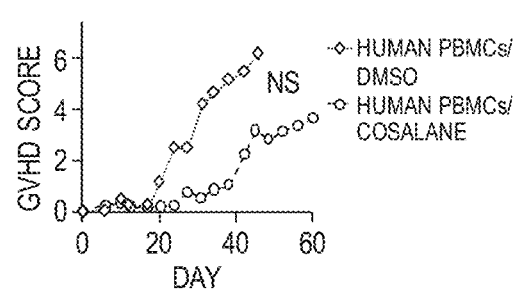
Figure 5G:
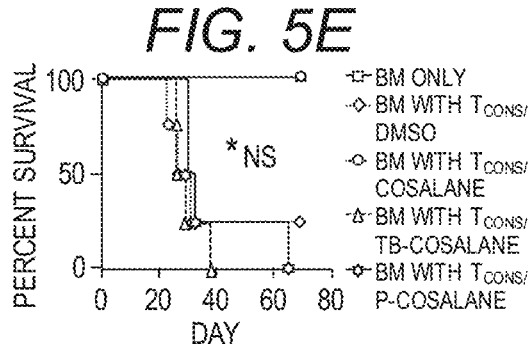
Figure 5H:
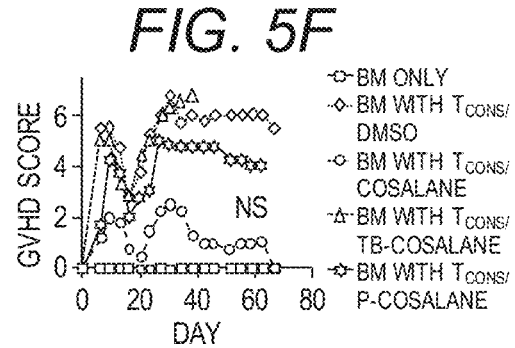
Figure 5I:
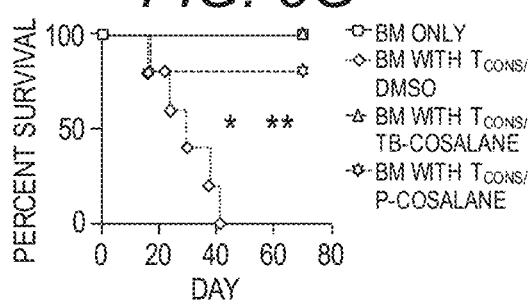
Figure 5J:
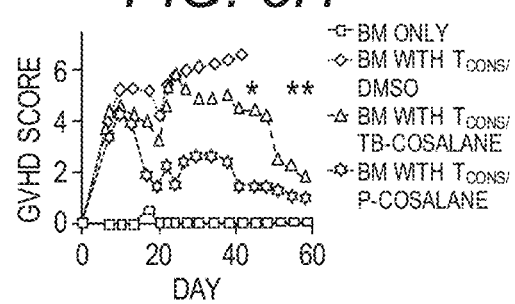

Previously we found cosalane to afford near complete aGVHD protection in a B6 into BALB/c system at a higher incubation concentration of 30 µg/ml (FIGS. 5C and 5D). As a result, we repeated our CCR7$^{-/-}$ B6 into BALB/c transplant but pre-incubated the donor $T_{cons}$ with an identical cosalane strength of 30 µg/ml. As depicted in FIGS. 7C and 7D, cosalane's effects were again much less complete in the absence of donor $T_{con}$ CCR7, even at a higher drug dose. Nevertheless, cosalane's protective effects were not entirely abrogated in this instance with recipients of cosalane treated CCR7$^{-/-}$ B6 $T_{cons}$ demonstrating longer survival times and a trend for lower aGVHD scores compared to control mice. Collectively these data indicated that cosalane does indeed exert its protective effects in a CCR7 associated manner. However, its modest residual efficacy even in the absence of the receptor suggests activity against additional target(s) yet to be determined.

In light of these survival data linking cosalane's ability to attenuate aGVHD to CCR7, we revisited our initial hypothesis that cosalane might impair donor $T_{con}$ trafficking into host lymphoid sites. Our previous in vivo trafficking measurements were performed on HSCT days +7 and +14 (FIGS. 6C and 6D) and failed to show any differences in lymphoid accumulation between cosalane and vehicle treated $T_{cons}$. It should be noted, however, that significant $T_{con}$ activation and expansion would have already occurred by these time points. Furthermore, donor immune cells could have recirculated back into the LNs via the afferent lymphatics. As a result, subtle cosalane effects on early lymphocyte trafficking out of the bloodstream might have been overlooked. In order to more definitively ascertain whether cosalane could impair donor $T_{con}$ homing into host SLT, we transplanted irradiated B6D2 recipients with cosalane or DMSO treated eGFP $T_{cons}$ but then harvested their organs for analysis by anti-eGFP ELISA after only 36 hours, a time point when $T_{con}$ expansion and/or recirculation would be minimal. Notably, an ELISA approach is extremely sensitive and allows for direct eGFP quantitation within post-irradiation, atrophied lymphoid sites without the need for the pooling of tissues. As shown in FIG. 7E, at this time point we detected a significant reduction in donor $T_{con}$ numbers within the spleen, ILN, and MLN in those mice given cosalane treated cells. Thus, cosalane does indeed limit the trafficking of donor $T_{cons}$ into host lymphoid sites early after transplant. The observed differences in donor $T_{con}$ numbers within SLT become less prominent over time, however, and are no longer detectable by the end of the first transplant week.

Cosalane Attenuates aGVHD while Sparing GVL Effects

Figure 8:
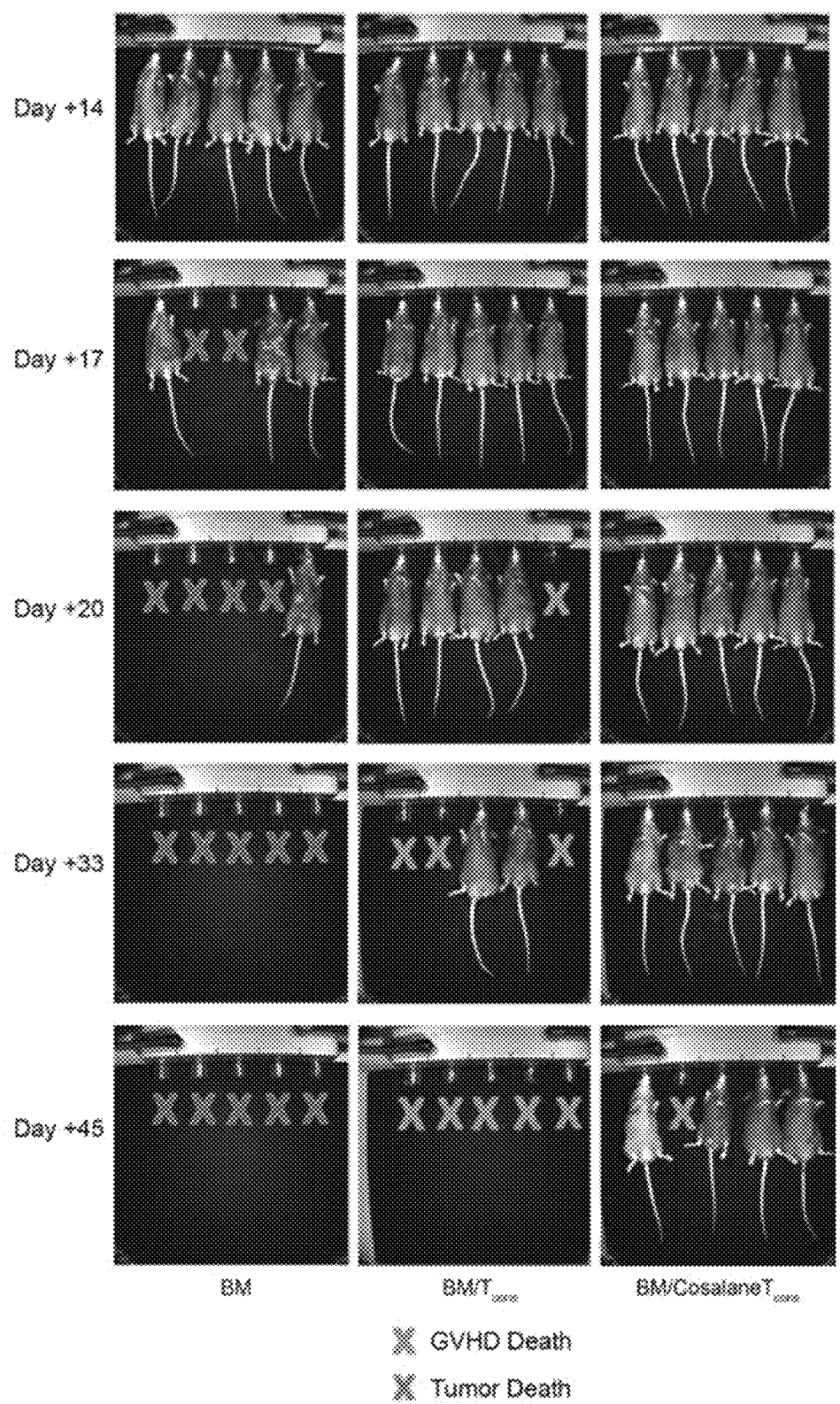
FIG. 8 shows cosalane treated $T_{cons}$ remain capable of GVL effects. B6D2 mice were lethally irradiated on transplant day −1. On day 0 recipients were administered $3 \times 10^6$ TCD B6 BM cells and $2.5 \times 10^4$ luciferase$^+$ P815 murine mastocytoma cells (H-2$^d$)+/−$4 \times 10^6$ B6 $T_{cons}$. Donor $T_{cons}$ were incubated ex vivo with DMSO vehicle or cosalane diluted in normal saline at 15 µg/ml. The cells were then mixed with untreated BM/tumor cells and administered immediately to recipient mice by tail vein injection. Mice were then serially imaged twice weekly following the intraperitoneal injection of luciferin. Selected imaging points are depicted. Recipient mortality was attributed to tumor versus aGVHD based on the tumor burden by imaging and clinical aGVHD scores at the time of death. Exposure time=4 seconds for all panels. N=5 per treatment group.

Any therapy that reduces aGVHD also has the potential to impair beneficial GVL effects. As a result, we evaluated cosalane's effects on GVL immunity using a well described P815 murine mastoma (H-2$^d$) leukemia model. Here, B6D2 mice were lethally irradiated and then administered 3×10$^6$ TCD B6 bone marrow cells containing 25,000 luciferase transfected P815 cells +/−4×10$^6$ B6 $T_{cons}$ to drive a GVL response. One half of those mice receiving BM/Tumor plus $T_{cons}$ were administered $T_{cons}$ incubated with DMSO and the other one half received cosalane treated $T_{cons}$. Recipients were subsequently evaluated by serial in vivo imaging in order to monitor tumor growth in each treatment group. In most instances recipient mortality could be reasonably attributed to tumor versus aGVHD based on the tumor burden by imaging and clinical aGVHD scores at the time of death. As depicted in FIG. 8, those mice given BM cells plus tumor without $T_{cons}$ all demonstrated aggressive tumor growth with 100% malignancy related mortality. Those mice given BM/Tumor plus DMSO treated $T_{cons}$ (BM/$T_{cons}$) all rejected the P815 inoculum but developed aggressive aGVHD. In contrast, those mice given BM/Tumor plus cosalane treated $T_{cons}$ (BM/Cosalane $T_{cons}$) demonstrated a substantial suppression of tumor growth and the longest overall survival times.

Figure 9:
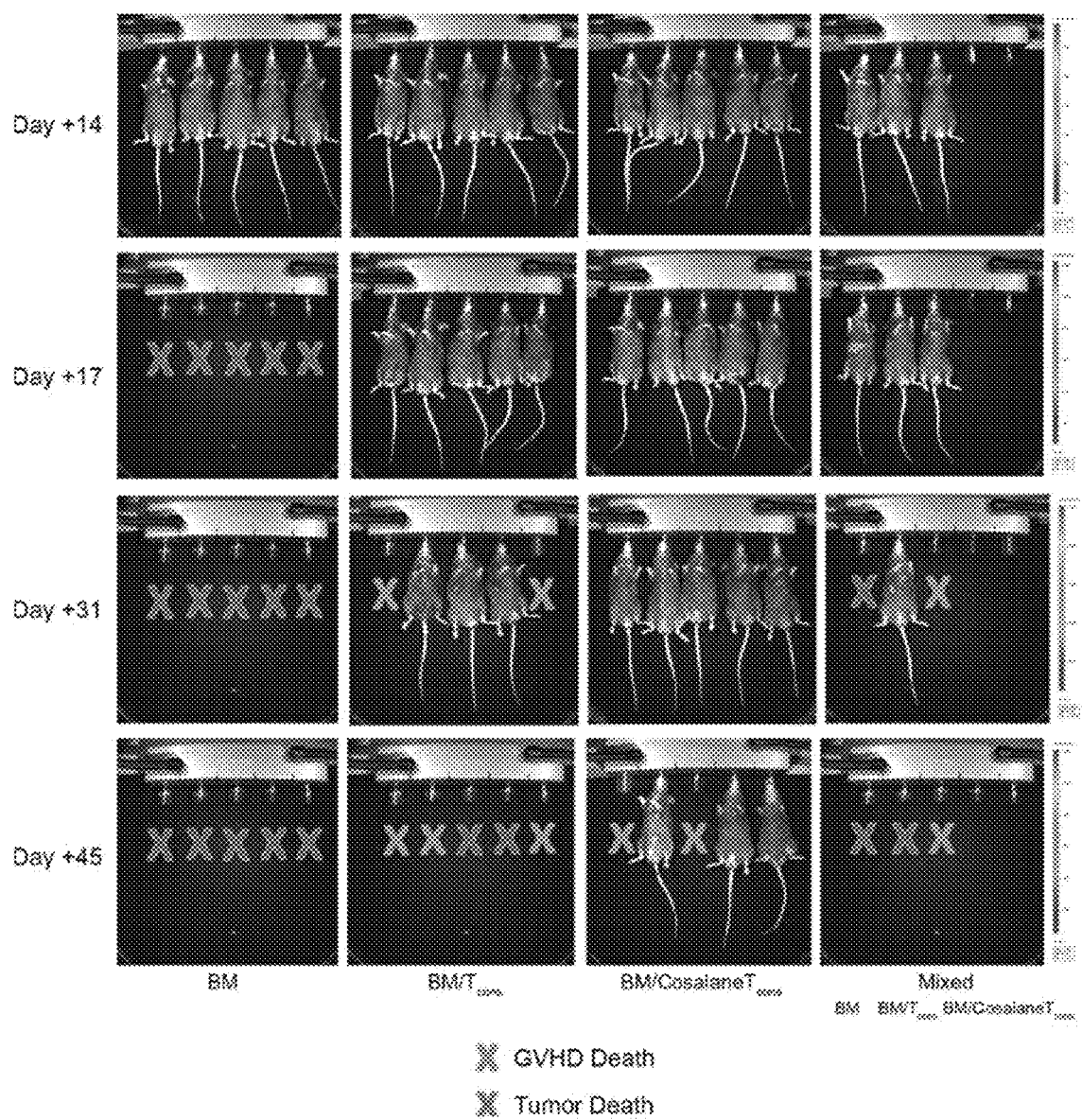
FIG. 9 shows cosalane treatment separates aGVHD from GVL effects in a P815 tumor model. B6D2 mice were lethally irradiated on transplant day −1. On day 0 recipients were administered $3 \times 10^6$ TCD B6 BM cells and $2.5 \times 10^4$ luciferase$^+$ P815 murine mastocytoma cells. Some recipients also received $2 \times 10^6$ DMSO treated B6 $T_{cons}$ or $4 \times 10^6$ cosalane treated B6 $T_{cons}$ (15 µg/ml). Mice were then serially imaged twice weekly following the intraperitoneal injection of luciferin. Selected imaging points are depicted. Exposure time=4 seconds for all panels. The "mixed" cage on the far right contained one mouse each of the BM/P815 only, BM/P815 plus DMSO $T_{cons}$, and BM/P815 plus cosalane $T_{cons}$ groups. N=6 per treatment group.

In GVL transplantation experiments the aGVHD control group (BM/Tumor/DMSO treated $T_{cons}$ in this instance) frequently succumbs to lethal aGVHD before any tumor growth can occur. As a result, it is often difficult to compare longer term GVL effects between these mice and mice given BM/$T_{cons}$ plus an anti-aGVHD therapy (BM/Tumor/cosalane treated $T_{cons}$) In order to address this, we performed a similar experiment but reduced the dose of $T_{cons}$ in the DMSO control group by 50%. Specifically, mice received 3×10$^6$ TCD BM cells plus 25,000 P815 cells, BM/Tumor plus 2×10$^6$ DMSO treated $T_{cons}$, or BM/Tumor plus 4×10$^6$ cosalane treated $T_{cons}$. As shown in FIG. 9, all mice given BM alone once again died from malignancy. 3/6 mice given 2×10$^6$ DMSO $T_{cons}$ died of tumor and 3/6 died of aGVHD. 3/6 mice given 4×10$^6$ cosalane treated $T_{cons}$ died of aGVHD and none succumbed to malignancy. Thus, in this transplant cosalane treated $T_{cons}$ generated an aGVHD response roughly equivalent to half as many untreated $T_{cons}$ while simultaneously producing a stronger GVL effect. These data indicated that cosalane was able to separate aGVHD effects from GVL effects in this model system.

Cosalane is Active Against Murine Cytomegalovirus and Epstein Barr Virus In Vitro Cosalane was originally developed as an anti-HIV therapeutic and appeared to function by blocking viral attachment through the disruption of viral gp190 binding to CD4 (Cushman et al., *J. Med. Chem.* 37:3040 (1994)). However, the compound was also shown to block viral cytopathic effect induced by a range of herpes viruses including herpes simplex 1 and 2 and human cytomegalovirus (Cushman et al., *J. Med Chem.* 38(3):443 (1995)). Notably, all are important pathogens in the human HSCT population. Based on these data, we performed additional experiments to determine if the compound was active against murine cytomegalovirus (mCMV), a surrogate for human CMV and a pathogen more amenable to eventual study in vivo. In addition, we evaluated cosalane for anti-EBV activity, another important member of the herpes virus family against which the compound had never before been evaluated.

Initial work focused on whether cosalane could limit the infection of murine fibroblasts by mCMV in vitro. Given our data showing that cosalane could significantly reduce aGVHD following an isolated ex vivo incubation step without systemic administration, we began by determining if cosalane could similarly impair mCMV infection by pretreating 3T3 murine fibroblast target cells with compound. With an isolated pretreatment of the 3T3 cells, cosalane had virtually no effect on the ability of mCMV to induce a visible cytopathic effect.

Figure 10A:
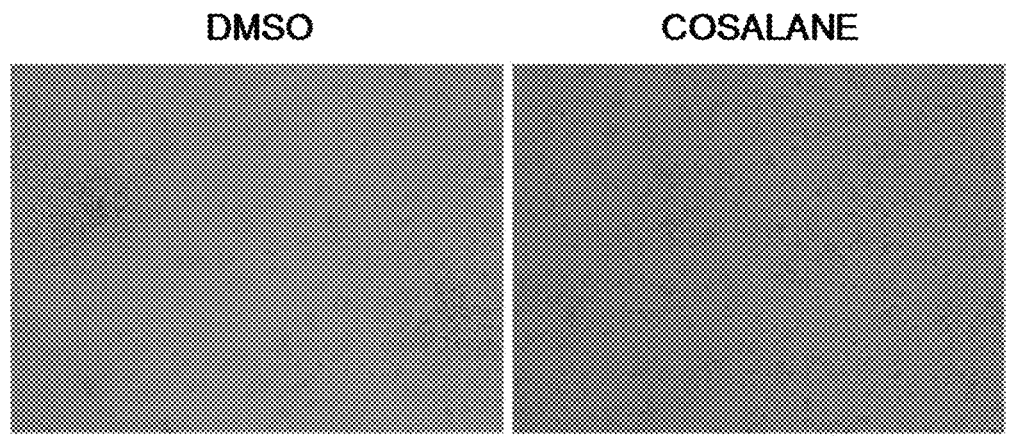
FIGS. 10A-10D show cosalane prevents mCMV cytopathic effect in vitro and blocks EBV entry into human cells. (A-C) Murine 3T3 fibroblasts were cultured in 6 well plates to 80 percent confluency. They were subsequently washed and incubated with mCMV infectivity media in the presence of 15 µg/ml of cosalane, p-cosalane, tb-cosalane or an equal volume of DMSO vehicle. The cells were then cultured overnight at 37° C. The following day the media was aspirated off and the cells were layered with viscous medium. 6 days later the plates were visualized and plaque number determined by microscopy. (A) Representative images of DMSO versus cosalane containing wells are depicted. (B) Viral multiplicity of infection=0.05. Average plaque numbers per well are indicated. *P=0.010 for mean plaque number comparison between DMSO and cosalane groups by Student's t test. P=0.0155 for comparison between DMSO and p-cosalane groups. *P=0.0106 for comparison between DMSO and tb-cosalane groups. (C) Viral multiplicity of infection=0.005. *P=0.04. P=0.050. *P=0.0418. (D) Human Raji cells were preincubated with cosalane or DMSO in serum free media for one hour, washed, and then cultured in GFP$^+$EBV infectivity media containing either DMSO vehicle or cosalane at 20 µg/ml. Thus, cosalane was entirely absent during the infection procedure (EBV/DMSO), present during the preincubation step only before the addition of virus (EBV/cosalane pretreatment only), or present throughout the entire infection procedure (EBV/cosalane throughout). Additional Raji cells were preincubated with p-cosalane or tb-cosalane, washed, and then infected with GFP$^+$EBV in media containing the respective compound at 20 µg/ml (both cosalane derivatives were present throughout the entire infection procedure). The cells were subsequently evaluated for infection (GFP$^+$) after 48 hours by flow cytometry. *P=0.008 for comparison of EBV/DMSO and EBV/cosalane pretreatment only groups by Student's t test. P=0.0055 for comparison of EBV/DMSO and EBV/cosalane throughout groups. *P=0.0237 for comparison between EBV/DMSO and EBV/p-cosalane groups. P>0.05 for comparison between EBV/DMSO and EBV/tb-cosalane groups.
Figure 10B:
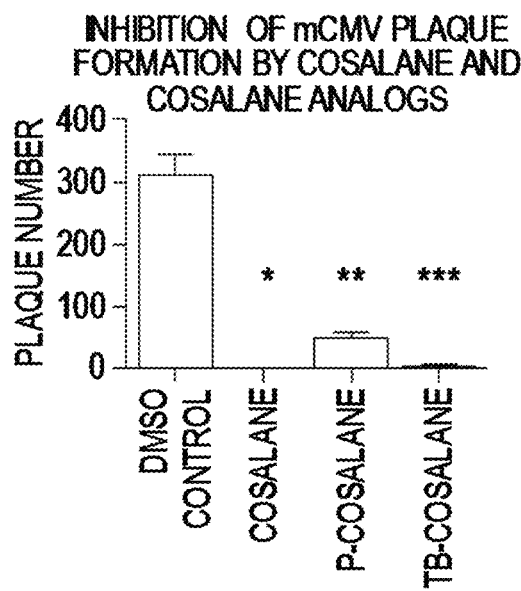
Figure 10C:
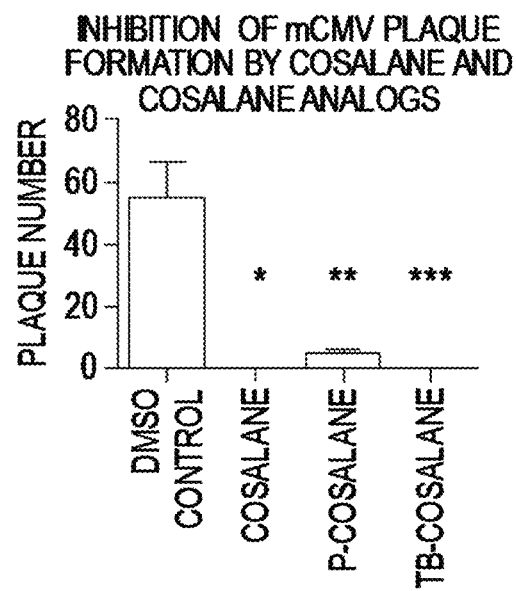

Following up on these data, we performed a similar transplant but added cosalane to the mCMV infectivity media at a concentration of 15 µg/ml. Thus, cosalane was present in solution throughout the entire virus infection period. In addition, we similarly examined the anti-viral activity of two cosalane analogues, p-cosalane and tb-cosalane. As depicted in FIGS. 10A-10C, cosalane limited viral cytopathic effect (FIG. 10A) and significantly reduced plaque number versus DMSO vehicle at two separate viral dilutions (FIGS. 10B and 10C). Similarly, both p-cosalane and tb-cosalane were active against mCMV although to a somewhat lesser degree versus the parent compound. Since a visible cytopathic effect occurs early after mCMV entry, these data implied an ability for the compounds to block either viral entry or production/activity of the virus's immediate early proteins.

Figure 10D:
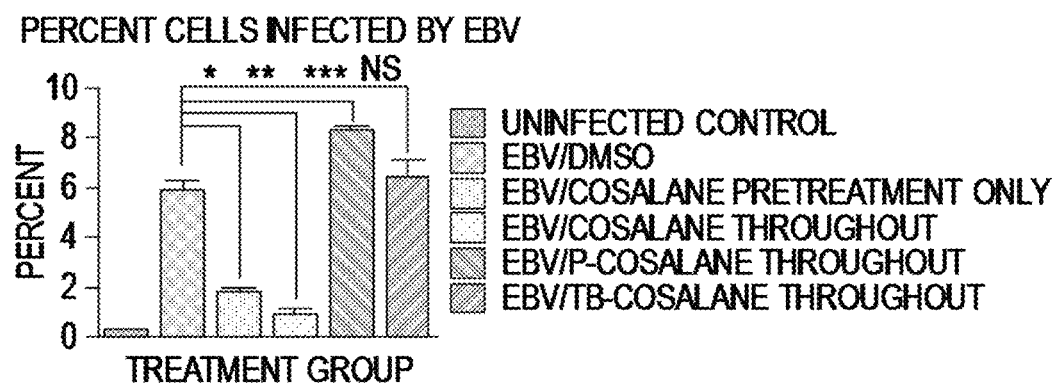

Next we evaluated whether cosalane could limit the infection of human cells by EBV. For this work human Raji cells, a Burkitt's lymphoma line, were pretreated with cosalane and then washed. The cells were then cultured in fresh media containing GFP+ EBV with or without additional cosalane in solution. In this way we could determine by flow cytometry whether cosalane could limit EBV viral entry and/or early transcription in vitro and whether an isolated pretreatment approach alone could afford any direct anti-viral protection. As depicted in FIG. 10D, cosalane significantly limited EBV infectivity when present in solution throughout the culture period. Furthermore, the isolated pretreatment of EBV target cells also reduced viral infection to a significant degree. In contrast, neither p-cosalane nor tb-cosalane appeared to possess any anti-EBV activity, even when present in solution. Collectively, these data indicated that cosalane could limit both mCMV and EBV infection in vitro but appeared to do so via different mechanisms. Furthermore, these effects did not appear to be a generalized class effect as both p-cosalane and tb-cosalane were less potent against mCMV and exhibited no inhibitory effect on EBV activity.

Discussion

Cosalane was originally developed as a novel HIV therapeutic. The drug appeared initially to be quite promising with activity against multiple strains of resistant HIV and a range of enveloped viruses relevant to the HSCT setting. Cosalane has never been used clinically, however, likely due to several important characteristics of the molecule. Cosalane exhibits very poor oral bioavailability (Kuchimanchi et al., *Drug Metab. Dispos.* 28(4):403 (2000)) which would have generally precluded its use as a viable anti-HIV therapy. Furthermore, while the drug can be successfully administered intravenously, it exhibits high albumin avidity and a propensity to accumulate within the liver (Kuchimanchi et al., *Drug Metab. Dispos.* 28(4):403 (2000); Kuchimanchi et al., *J. Pharm. Sci.* 90(5):659 (2001)). Despite these drawbacks, however, the HSCT setting represents a unique clinical scenario in which the compound could be effectively utilized. Specifically, HSCT allows for the ex vivo manipulation of donor cells prior to their administration. As a result, the bioavailability and pharmacokinetic concerns that have thus far limited cosalane's clinical translation would be much less of an issue. At this time, we envision the compound being applicable to the stem cell transplantation field in one of several ways. First, since cosalane diminishes aGVHD by acting on donor $T_{cons}$, the compound could be used to limit the aGVHD potential of donor lymphocyte infusions (DLI) undertaken to boost donor chimerisms and/or stave off early malignancy recurrence. Our own data suggest that cosalane specifically limits the ability of donor $T_{cons}$ to accumulate in the gastrointestinal tract and liver, important sites of aGVHD development following DLI, while sparing the GVL potential of these cells. Second, cosalane could be used as an aGVHD prophylactic approach at the time of HSCT. Based on our data, it would appear that an entire hematopoietic stem cell product could be safely treated with drug without any detrimental effects on engraftment. Finally, cosalane could offer the potential for anti-viral prophylaxis after transplant. In the current study an isolated incubation of human cells with cosalane appeared to shield them from subsequent EBV infection. This implies that the ex vivo treatment of a donor stem cell product prior to transplant might theoretically insulate the engrafting cells from host viral reactivation. Nevertheless, we realistically expect that the drug would need to be dosed systemically to HSCT recipients post-transplant in order to fully capitalize on the compound's anti-viral properties. As a result, applying the compound as an anti-infectious agent would appear to be a less immediate therapeutic possibility. However, efforts are currently ongoing at our center to develop a nano-particle version of the drug in order to address its pharmacokinetic limitations and to optimize its systemic administration.

Cosalane came to our group's attention during a search for small molecule antagonists of CCR7, a chemokine receptor critical for aGVHD pathogenesis (Hull-Ryde et al., *SLAS Discovery* 2018. Jun. 1. Epub ahead of print). Nevertheless, cosalane's mechanism of action in attenuating aGVHD is incompletely understood. Previously, we demonstrated that $CCR7^{-/-}$ $T_{cons}$ possessed an impaired ability to traffic to and expand within host secondary lymphoid tissue. This in turn resulted in reduced $T_{con}$ accumulation within the colon and liver by the second post-transplant week[1]. In the current study, cosalane treated donor $T_{cons}$ similarly demonstrated an impaired ability to traffic into host SLT early after transplant and accumulated to a lesser degree within gastrointestinal and hepatic tissues by transplant day +14. Furthermore, studies using CCR7$^{-/-}$ T$_{cons}$ demonstrated that the compound was considerably less effective in limiting aGVHD when donor T$_{cons}$ lacked this particular receptor. Collectively, all of these data suggested that CCR7 is indeed an important cosalane drug target in the HSCT setting. Nevertheless, several of our findings imply activity against other receptors beyond CCR7. Cosalane's effects on T$_{con}$ trafficking into SLT were rather modest, with treated and untreated cells accumulating to similar degrees within host ILNs, MLNs, and spleen by transplant day +7. Furthermore, cosalane demonstrated some residual efficacy in limiting aGVHD even when donor T$_{cons}$ were knocked out at CCR7. As described above, cosalane was originally developed as anti-viral agent. However, the drug was previously shown to block CCR1 dependent chemotaxis in response to CCL5 (RANTES) (Howard et al., *Bioorg. Med. Chem. Lett.* 11(1):59 (2001)). This is potentially quite relevant to our own findings as CCR1 was previously shown to be critical for gastrointestinal aGVHD in mouse transplant models (Choi et al., *Blood* 110(9):3447 (2007)). Based on currently available evidence, we suspect that cosalane attenuates aGVHD through its effects on CCR7 and one or more inflammatory chemokine receptors that may include CCR1.

Cosalane is a poor membrane penetrator and appears to imbed in the outer leaflet of artificial phospholipid bilayers by way of its cholestane moiety (Pal et al., *J. Pharm. Sci.* 89(6):826 (2000)). Given its negatively charged carboxylic head groups, it is therefore possible that cosalane could exert its effects at the cell surface via completely non-specific charge alterations resulting in impaired cell adhesion, changes in cell shape, or generally impaired receptor signaling. Alternatively, the cholestane portion of the molecule could conceivably modify membrane fluidity and thus affect cell function in another non-specific manner. Multiple findings, however, would seem to argue against either possibility. In previous work, we examined the ability of a range of different cholesterol derivatives to block CCR7 dependent chemotaxis. All were found to be inactive, arguing against a non-specific sterol effect on the membrane. Furthermore, we demonstrated that cosalane itself was approximately 10-fold more active against CCL19 versus CCL21, indicating that the nature of the particular receptor ligand was important for the compound's action (Hull-Ryde et al., *SLAS Discovery* 2018. Jun. 1. Epub ahead of print). Similarly, in previous work describing the compound's ability to block CCR1, the identity of the chemokine agonist critically influenced the compound's efficacy. Specifically, cosalane blocked CCR1 dependent chemotaxis in response to CCL5 but was inactive against the receptor's other two ligands, CCL3 and CCL4 (Howard et al., *Bioorg. Med. Chem. Lett.* 11(1):59 (2001)). Moreover, in the current study cosalane's ability to attenuate aGVHD after HSCT appeared to be linked to CCR7. Collectively, all of these findings indicate a complex range of activities that likely extend beyond a single target, but which appear to be confined to a limited number of particular receptor/ligand pairs.

In summary, our data indicate for the first time that the existing anti-viral drug cosalane possesses an ability to attenuate aGVHD in multiple murine HSCT model systems. More broadly, these studies are to our knowledge the first to demonstrate efficacy for cosalane in a relevant animal model, and the first to show that a CCR7 small molecule antagonist can improve disease outcomes in a preclinical system.

The foregoing is illustrative of the present invention, and is not to be construed as limiting thereof. The invention is defined by the following claims, with equivalents of the claims to be included therein.

That which is claimed is:

1. A method for modifying hematopoietic stem cells to decrease the risk of developing graft versus host disease following transplantation of the cells into a subject, comprising contacting the hematopoietic stem cells with an effective amount of a compound of Formula I or Formula II or a pharmaceutically acceptable salt or prodrug thereof:

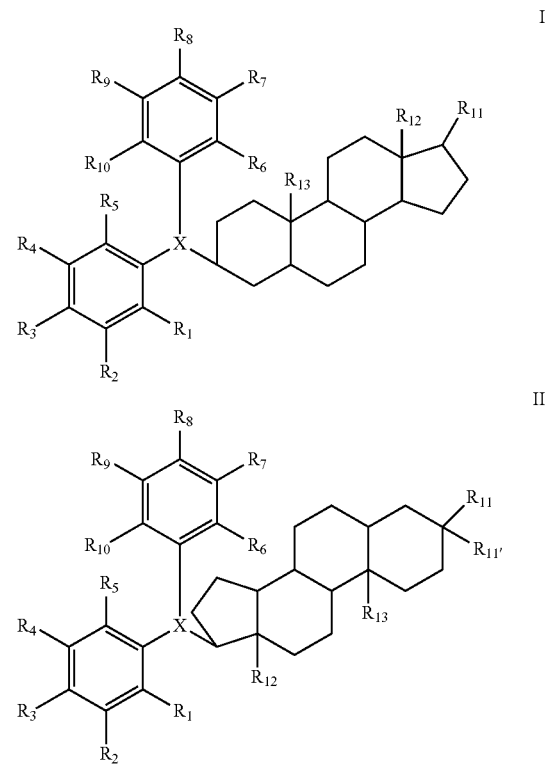

wherein
R$_1$ to R$_{11}$ and R$_{11'}$ are independently H, halogen, hydroxy, amino, C$_1$-C$_5$ alkoxy, benzoyloxy, R$_{14}$C(O)O, COOH or a salt thereof, SO$_3$H or a salt thereof, PO$_3$H$_2$ or a salt thereof, C$_1$-C$_{24}$ alkyl, COOR$_{15}$, SO$_3$R$_{16}$, C(O)NR$_{17}$R$_{18}$, SO$_2$NR$_{19}$R$_{20}$, SR$_{21}$, SCH$_2$R$_{25}$, SC(O)R$_{21}$, NR$_{22}$R$_{23}$, NHC(O)—R$_{24}$, O(CH$_2$)$_n$—R$_{26}$—R$_{27}$, OC(O)N(H)C(H)(R$_{28}$)COOR$_{29}$;
R$_{12}$ and R$_{13}$ are C$_1$-C$_7$ alkyl groups;
R$_{14}$ is H or C$_1$-C$_5$ alkyl;
R$_{15}$ is aryl or C$_1$-C$_5$ alkyl;
R$_{16}$ is aryl or C$_1$-C$_5$ alkyl;
R$_{17}$ and R$_{15}$ are each independently H, C$_1$-C$_5$ alkyl, aryl or hydroxy;
R$_{19}$ and R$_{20}$ are each independently H, C$_1$-C$_5$ alkyl or aryl;
R$_{21}$ is C$_1$-C$_5$ alkyl or aryl;
R$_{22}$ and R$_{23}$ are each independently H, C$_1$-C$_5$ alkyl or aryl;
R$_{24}$ is aryl optionally substituted with COOH or a salt thereof, or C$_1$-C$_7$ alkoxy;
R$_{25}$ is aryl;
R$_{26}$ is aryl;
R$_{27}$ is COOH or a salt thereof, B(OH)$_2$ or a salt thereof, nitro, C$_1$-C$_7$ alkoxy or aryl, wherein the aryl is substituted with COOH or a salt thereof, B(OH)$_2$ or a salt thereof, nitro or C$_1$-C$_7$ alkoxy;
R$_{28}$ is an amino acid side chain;
R$_{29}$ is H or C$_1$-C$_4$ alkyl;
X is a (C$_1$-C$_7$ alkylene) or (C$_1$-C$_7$ alkylene)C(O)NH; and n is 1 to 7;
thereby decreasing the risk of developing graft versus host disease following transplantation of the cells.

2. A method for decreasing the risk of developing graft versus host disease following transplantation of a graft comprising hematopoietic stem cells in a subject in need thereof, comprising contacting the graft with an effective amount of a compound of Formula I or Formula II or a pharmaceutically acceptable salt or prodrug thereof:

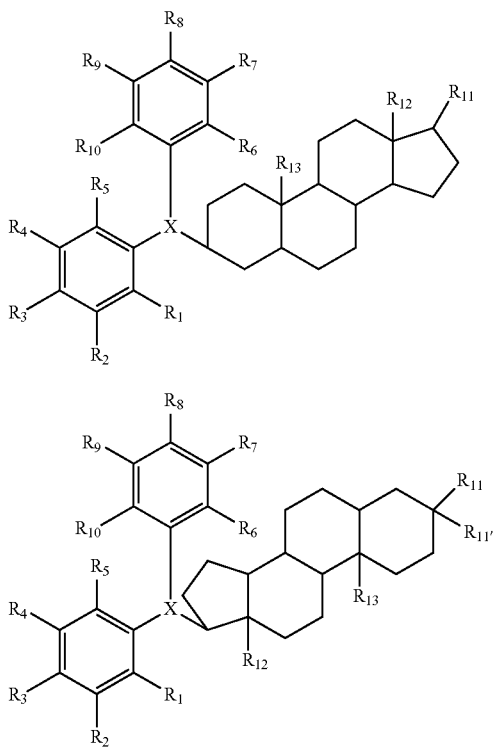

wherein
R$_1$ to R$_{11}$ and R$_{11}$' are independently H, halogen, hydroxy, amino, C$_1$-C$_5$ alkoxy, benzoyloxy, R$_{14}$C(O)O, COOH or a salt thereof, SO$_3$H or a salt thereof, PO$_3$H$_2$ or a salt thereof, C$_1$-C$_{24}$ alkyl, COOR$_{15}$, SO$_3$R$_{16}$, C(O)NR$_{17}$R$_{18}$, SO$_2$NR$_{19}$R$_{20}$, SR$_{21}$, SCH$_2$R$_{25}$, SC(O)R$_{21}$, NR$_{22}$R$_{23}$, NHC(O)—R$_{24}$, O(CH$_2$)$_n$—R$_{26}$—R$_{27}$, OC(O)N(H)C(H)(R$_{28}$)COOR$_{29}$;
R$_{12}$ and R$_{13}$ are C$_1$-C$_7$ alkyl groups;
R$_{14}$ is H or C$_1$-C$_5$ alkyl;
R$_{15}$ is aryl or C$_1$-C$_5$ alkyl;
R$_{16}$ is aryl or C$_1$-C$_5$ alkyl;

R$_{17}$ and R$_{18}$ are each independently H, C$_1$-C$_5$ alkyl, aryl or hydroxy;
R$_{19}$ and R$_{20}$ are each independently H, C$_1$-C$_5$ alkyl or aryl;
R$_{21}$ is C$_1$-C$_5$ alkyl or aryl;
R$_{22}$ and R$_{23}$ are each independently H, C$_1$-C$_5$ alkyl or aryl;
R$_{24}$ is aryl optionally substituted with COOH or a salt thereof, or C$_1$-C$_7$ alkoxy;
R$_{25}$ is aryl;
R$_{26}$ is aryl;
R$_{27}$ is COOH or a salt thereof, B(OH)$_2$ or a salt thereof, nitro, C$_1$-C$_7$ alkoxy or aryl, wherein the aryl is substituted with COOH or a salt thereof, B(OH)$_2$ or a salt thereof, nitro or C$_1$-C$_7$ alkoxy;
R$_{28}$ is an amino acid side chain;
R$_{29}$ is H or a C$_1$-C$_4$ alkyl;
X is a (C$_1$-C$_7$ alkylene) or (C$_1$-C$_7$ alkylene)C(O)NH; and n is 1 to 7; and
transplanting the contacted graft into the subject;
thereby decreasing the developing risk of graft versus host disease.

3. The method of claim 1, wherein R$_1$, R$_5$, R$_6$ and R$_{10}$ are H, R$_2$ and R$_7$ are chlorine, R$_{11}$ is CH(CH$_3$)(CH$_2$)$_3$CH(CH$_3$)$_2$, R$_{12}$ and R$_{13}$ are methyl and X is C=CH(CH$_2$)$_2$.

4. The method of claim 3, wherein R$_3$ and R$_8$ are O(CH$_2$)$_n$—R$_{26}$—R$_{27}$, wherein n is 1, R$_{26}$ is phenyl, R$_{27}$ is selected from the group consisting of aryl, nitro, COOH or a salt thereof, B(OH)$_2$ or a salt thereof, C$_1$-C$_7$ alkoxy and combinations thereof, wherein the aryl of R$_{27}$ may be substituted with nitro, COOH or salt thereof, B(OH)$_2$ or a salt thereof, C$_1$-C$_7$ alkoxy and combinations thereof.

5. The method of claim 1, wherein R$_1$, R$_5$, R$_6$, R$_{10}$, R$_{11}$ and R$_{11}$' are H, R$_2$ and R$_7$ are chlorine, R$_{12}$ and R$_{13}$ are methyl and X is C—CH(CH$_2$)$_2$.

6. The method of claim 5 wherein R$_3$ and R$_8$ are hydroxy, and R$_4$ and R$_9$ are OC(O)N(H)C(H)(R$_{28}$)COOH, wherein R$_{28}$ is H, CH$_2$(CH)$_2$CH$_3$, CH$_2$Ph, CH$_2$COOH or a salt thereof, or CH$_2$CH$_2$COOH or a salt thereof.

7. The method of claim 1, wherein the compound of Formula I or Formula II is cosalane.

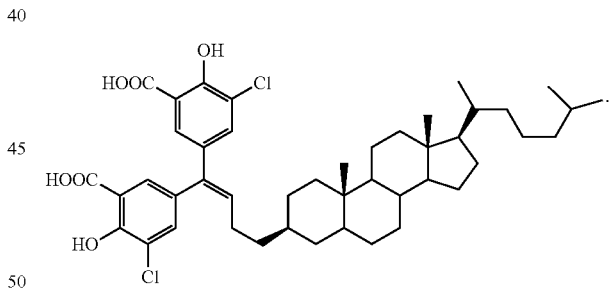

8. The method of claim 1, wherein the graft versus host disease is acute graft versus host disease.

9. The method of claim 1, wherein the graft is from bone marrow of a donor.

10. The method of claim 1, wherein the graft is from peripheral blood of a donor.

* * * * *

UNITED STATES PATENT AND TRADEMARK OFFICE
CERTIFICATE OF CORRECTION

PATENT NO. : 12,208,105 B2
APPLICATION NO. : 17/298776
DATED : January 28, 2025
INVENTOR(S) : Coghill et al.

It is certified that error appears in the above-identified patent and that said Letters Patent is hereby corrected as shown below:

In the Specification

Column 1, Lines 7-10: Please delete and replace with the following:
"This application is a 35 U.S.C. § 371 national phase application of PCT Application PCT/US2019/064207 filed December 3, 2019, which claims the benefit, under 35 U.S.C. § 119(e), of U.S. Provisional Application Serial No. 62/774,646, filed on December 3, 2018, the entire contents of each of which are incorporated by reference herein."

Column 1, Lines 14-19: Please delete and replace with the following:
"This invention was made with government support under HL111205 awarded by the National Institutes of Health. The government has certain rights in the invention."

Column 6, Line 55: Please correct "+601" to read --+60.--

Column 20, Lines 17-48: Please remove the indentation

Column 36, Line 10: Please correct "eGFP" to read --eGFP$^+$--

In the Claims

Column 40, Line 57, Claim 1: Please correct "$R_{17}$ and $R_{15}$" to read --$R_{17}$ and $R_{18}$--

Column 41, Line 49, Claim 2: Please correct "$R_{11'}$" to read --$R_{11'}$--

Column 42, Line 32, Claim 5: Please correct "C—CH(CH$_2$)$_2$" to read --C=CH(CH$_2$)$_2$--

Signed and Sealed this
Fifteenth Day of July, 2025

Coke Morgan Stewart
*Acting Director of the United States Patent and Trademark Office*